(12) United States Patent
Nesaretnam

(10) Patent No.: US 8,901,168 B2
(45) Date of Patent: Dec. 2, 2014

(54) VITAMIN E SUPPLEMENTATION TO TETANUS TOXOID

(76) Inventor: Kalanithi Nesaretnam, Kajang (MY)

( * ) Notice: Subject to any disclaimer, the term of this patent is extended or adjusted under 35 U.S.C. 154(b) by 1397 days.

(21) Appl. No.: 12/243,839

(22) Filed: Oct. 1, 2008

(65) Prior Publication Data

US 2009/0088467 A1 Apr. 2, 2009

(30) Foreign Application Priority Data

Oct. 2, 2007 (MY) ............... PI 20071689

(51) Int. Cl.
*A61K 31/355* (2006.01)

(52) U.S. Cl.
CPC .................................. *A61K 31/355* (2013.01)
USPC ......................... 514/458; 549/408

(58) Field of Classification Search
CPC .................................... A61K 31/355
USPC ......................... 514/458; 549/408
See application file for complete search history.

(56) References Cited

U.S. PATENT DOCUMENTS 6,656,358 B2 * 12/2003 May et al. ............ 210/635
2005/0281889 A1 12/2005 Chandra

FOREIGN PATENT DOCUMENTS

| EP | 1 818 388 | * | 8/2007 |
| EP | 1958629 A1 | | 8/2008 |
| WO | WO00/56361 | * | 9/2000 |

OTHER PUBLICATIONS

Meydani, M. Effect of functional food ingredients: vitamin E modulation of cardiovascular diseases and immune status in the elderly. Am. J. Clin. Nutr. 71 (suppl), 1665S-8S (2000).*
Nesaretnam et al. Tocotrienol-rich fraction from palm oil affects gene expression in tumors resulting from MCF-7 cell inoculation in athymic mice. Lipids 39(5), pp. 459-467 (2004).*
Meydani, Mohsen, "Vitamin E", The Lancet, vol. 345, Jan. 21, 1995, pp. 170-175.
Kutukculer et al., "Adequate immune response to tetanus toxoid and failure of vitamin A and E supplementation to enhance antibody response in healthy children", Vaccine 18, 2000, pp. 2979-2984.
Muir et al., "Dietary supplementation with vitamin E modulates avian intestinal immunity", British Journal of Nutrition, 2002, 87, pp. 579-585.
Meydani et al., "Vitamin E Supplementation and In Vivo Immune Response in Healthy Elderly Subjects", JAMA, May 7, 1997—vol. 277, No. 17, pp. 1380-1386.
Meydani et al., "Letter to the Editor—Vitamin E Supplementation and Immune Response in Elderly Patients", JAMA, Feb. 18, 1998—vol. 279, No. 7, pp. 505-510.
Prosecution History of EP2044936, (2008-2012).

* cited by examiner

*Primary Examiner* — Barbara P Badio
*Assistant Examiner* — Sara E Townsley
(74) *Attorney, Agent, or Firm* — Workman Nydegger

(57) ABSTRACT

The invention relates to a formulation for supplementation on immune response to a biological substance. More particularly, the formulation consists of one or more forms of Vitamin E which provides a supplementation on immune response to tetanus toxoid. In addition, the present invention also relates on the effect of different types of Vitamin E such as tocotrienol rich fraction, delta tocotrienol and alpha-tocopherol supplementation on immune response to tetanus toxoid vaccination.

4 Claims, 11 Drawing Sheets

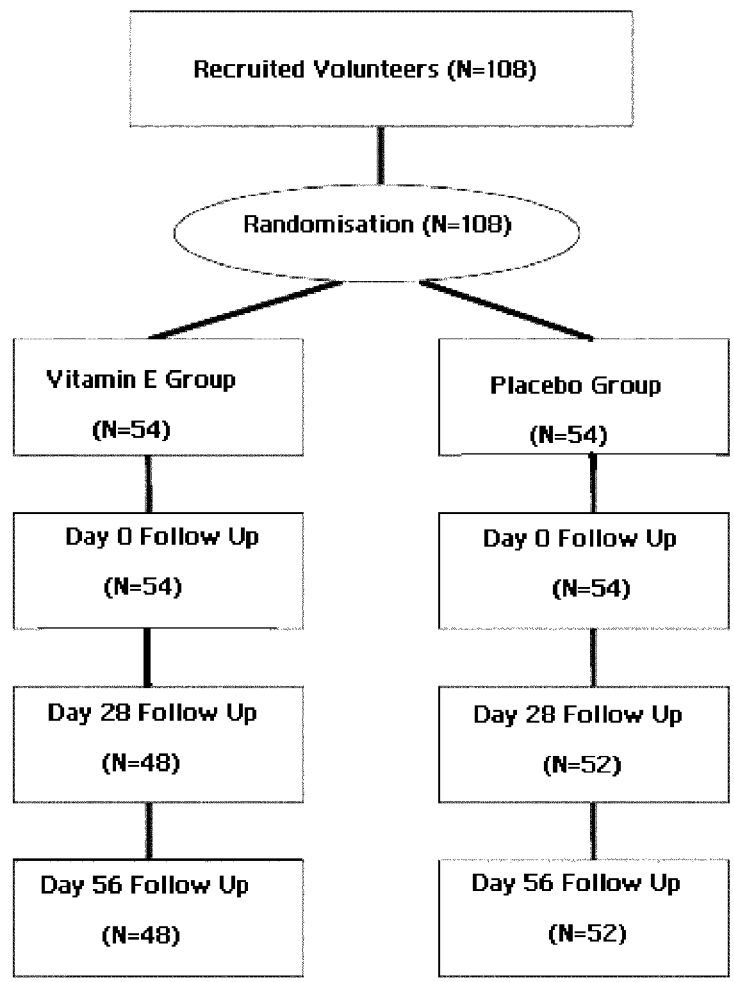
Figure1 Flow diagram illustrates the participant allocation and retention throughout the study

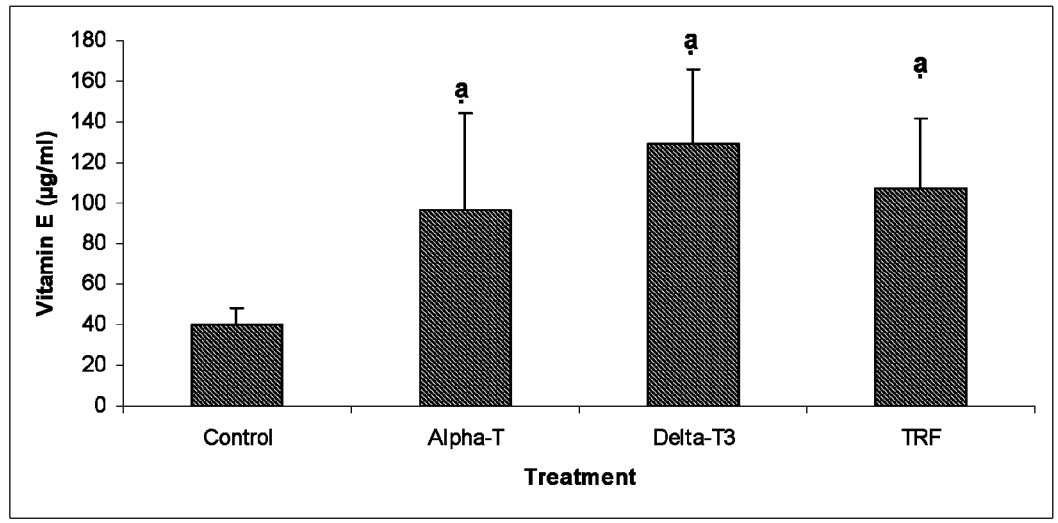
Figure-2: Concentrations of total vitamin E in the adipose tissue of mice supplemented with different isomers of vitamin E daily for 56 days.
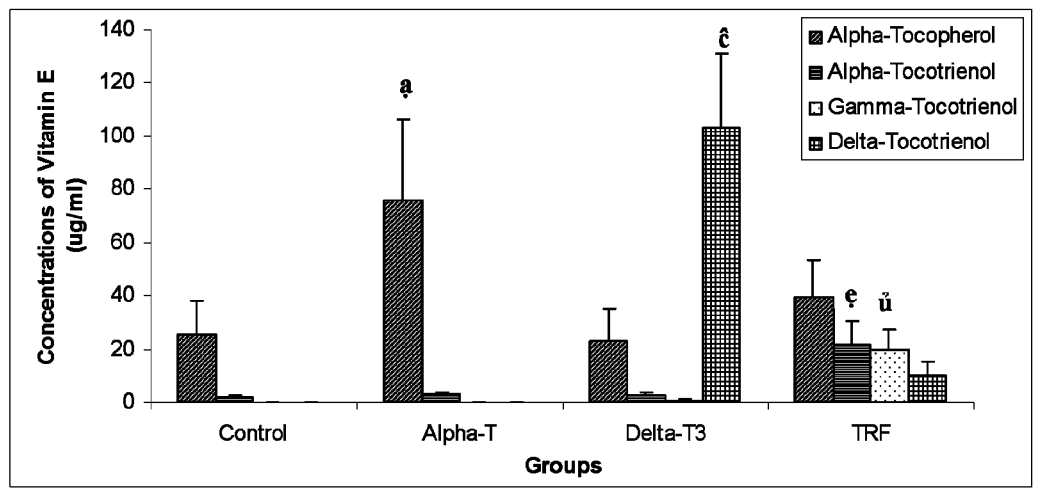
Figure-3: Concentrations of α-tocopherol and tocotrienols in the adipose tissue of mice supplemented with different isomers of vitamin E daily for 56 days.

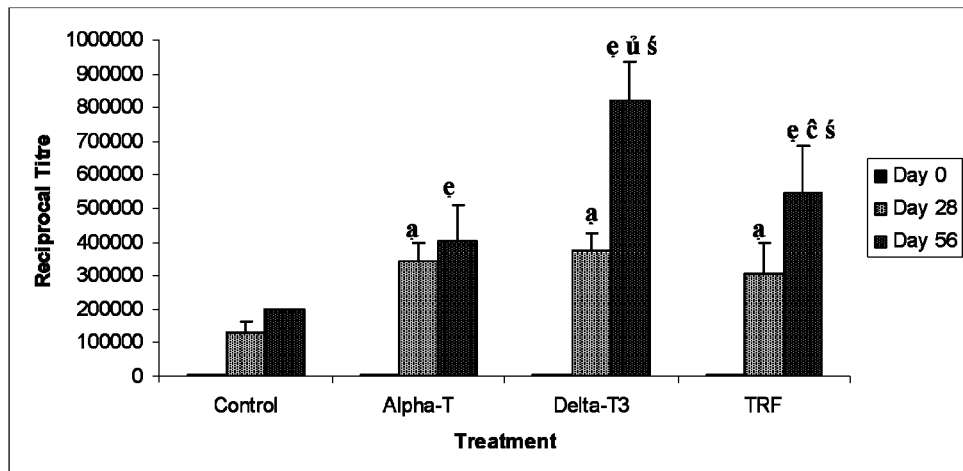
Figure-4.: Histogram comparing the total Ig anti-TT titres between control and vitamin E supplemented mice
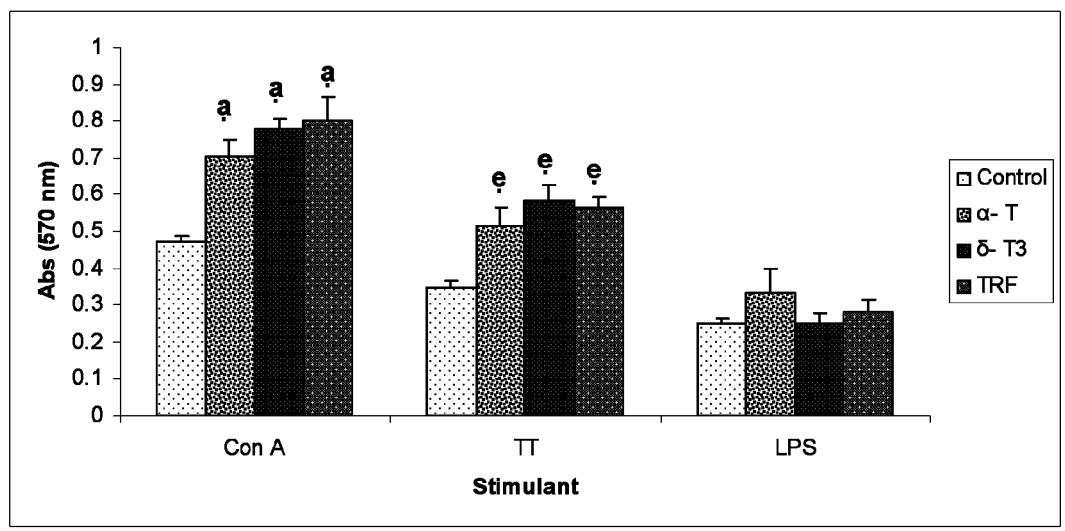
Figure-5: Effect of vitamin E supplementation on mitogen- (Con A and LPS) and Antigen-stimulated (TT) splenocyte proliferation in TT-immunised mice.

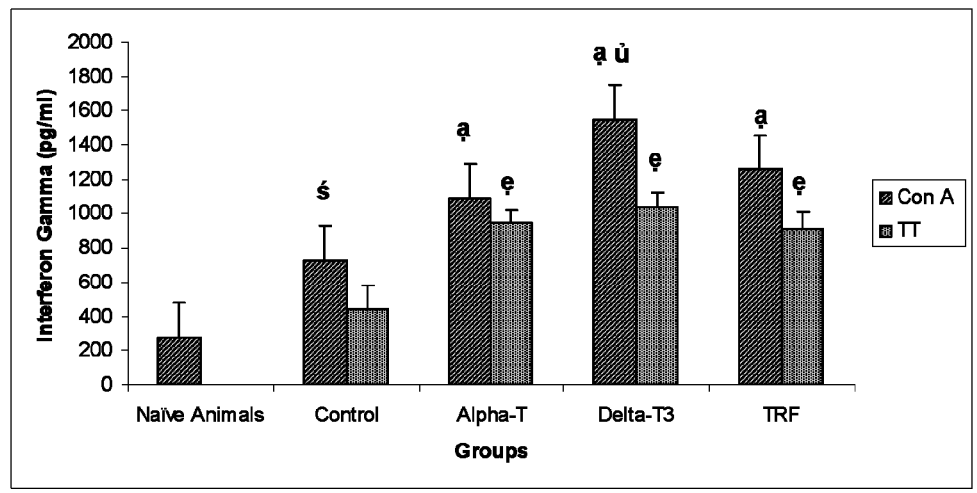
Figure-6: Effect of vitamin E supplementation on the production of IFN-□ by Con A- or TT-stimulated splenocytes
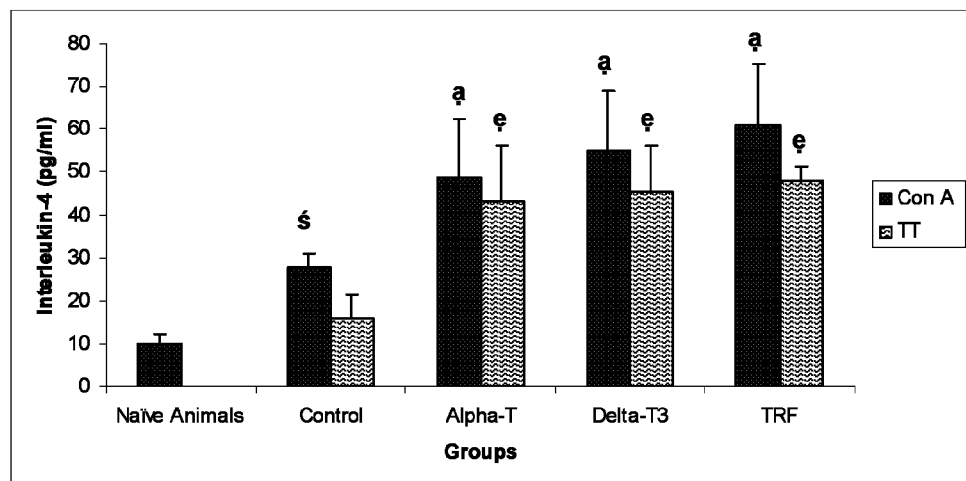
Figure-7: Effect of vitamin E supplementation on the production of IL-4 by Con A- or TT-stimulated splenocytes

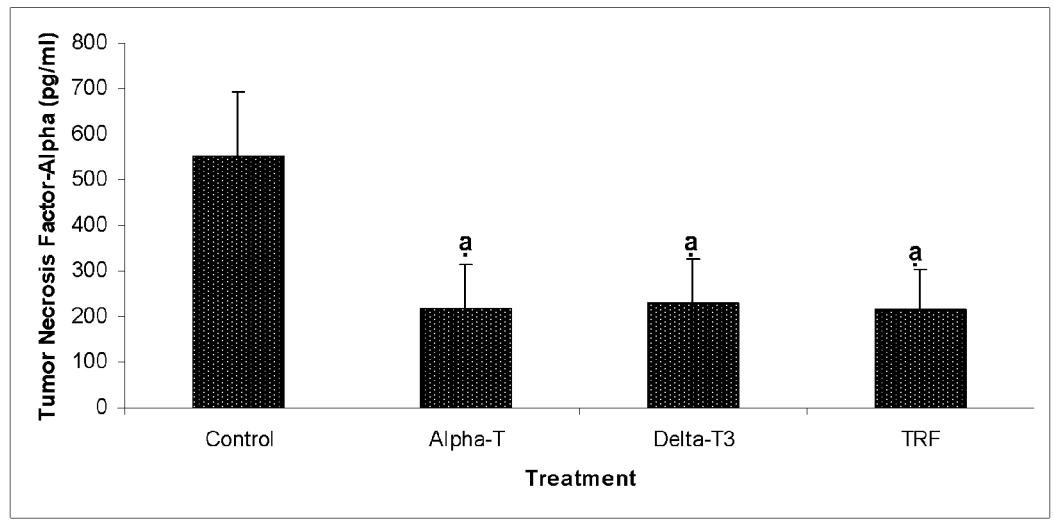
Figure-8: Effect of vitamin E supplementation on the production of TNF-α by LPS-stimulated splenocytes
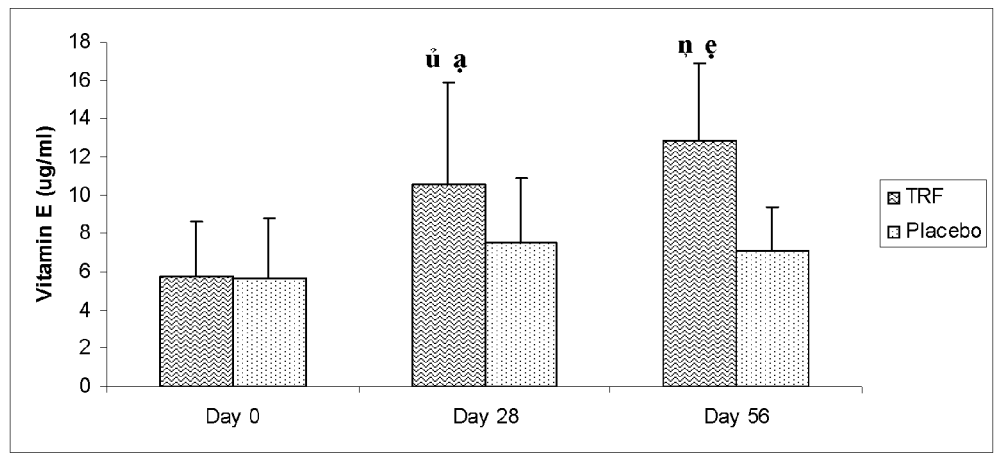
Figure-9: Concentration of total vitamin E in the plasma of control and experimental volunteers

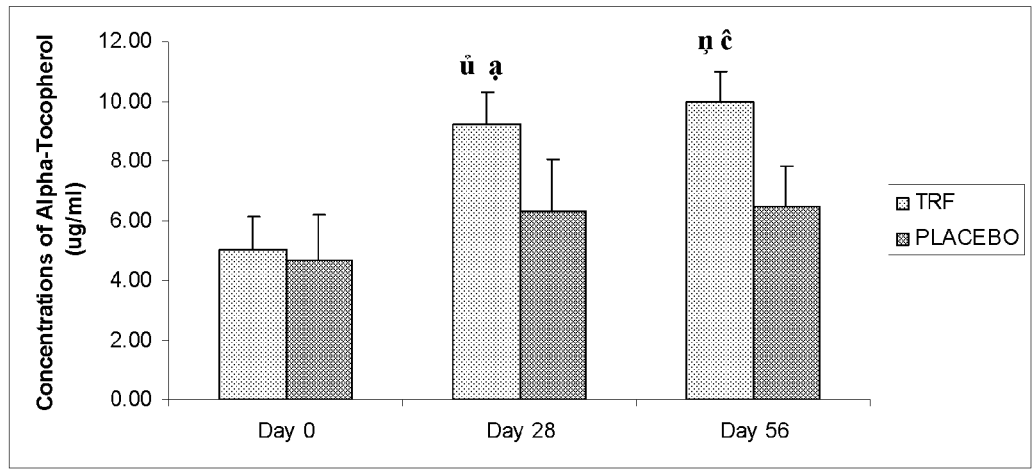
Figure-10: Concentration of total alpha-tocopherol in the plasma of control and experimental volunteers
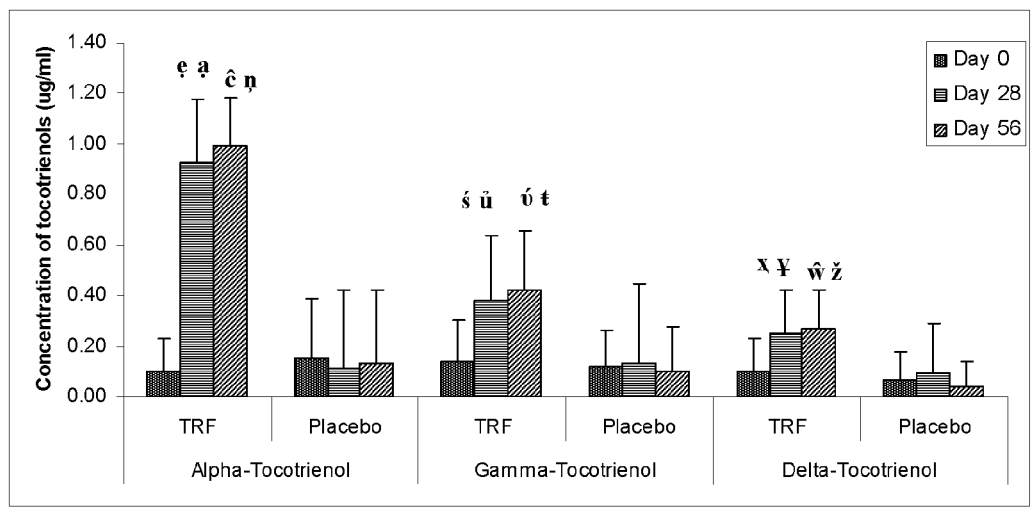
Figure-11: Concentration of tocotrienols in the plasma of control and experimental volunteers

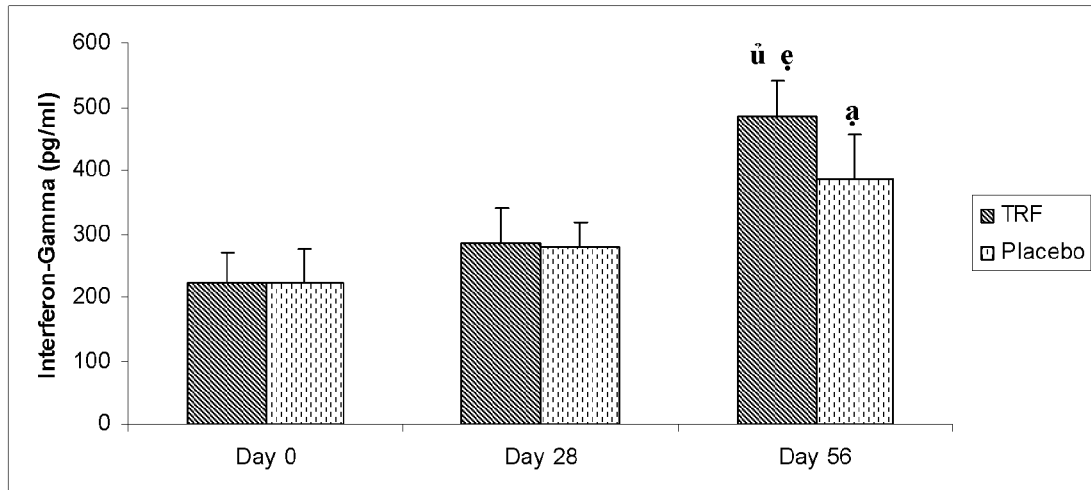
Figure-12: Effect of TRF supplementation on the production of IFN-γ by Con A stimulated PBMC
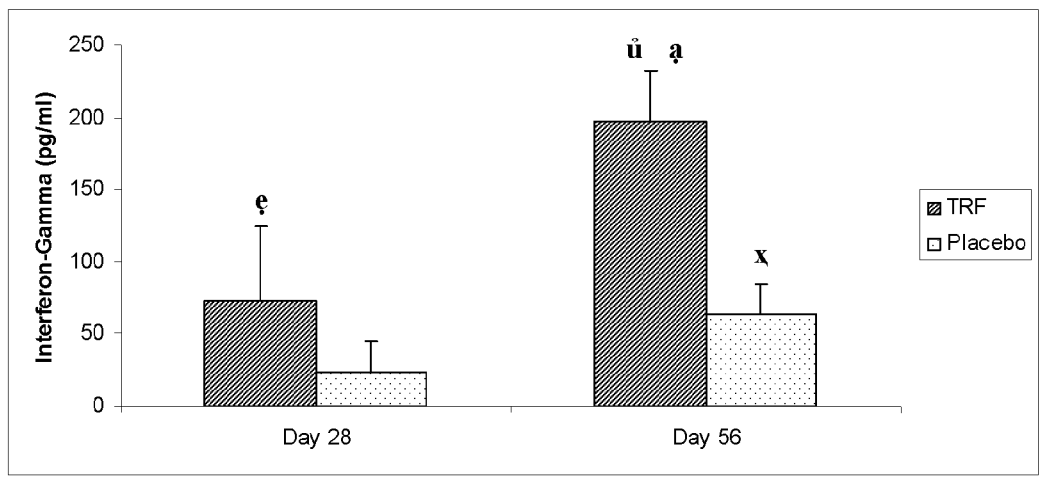
Figure-13: Effect of TRF supplementation on the production of IFN-γ by TT-stimulated PBMC

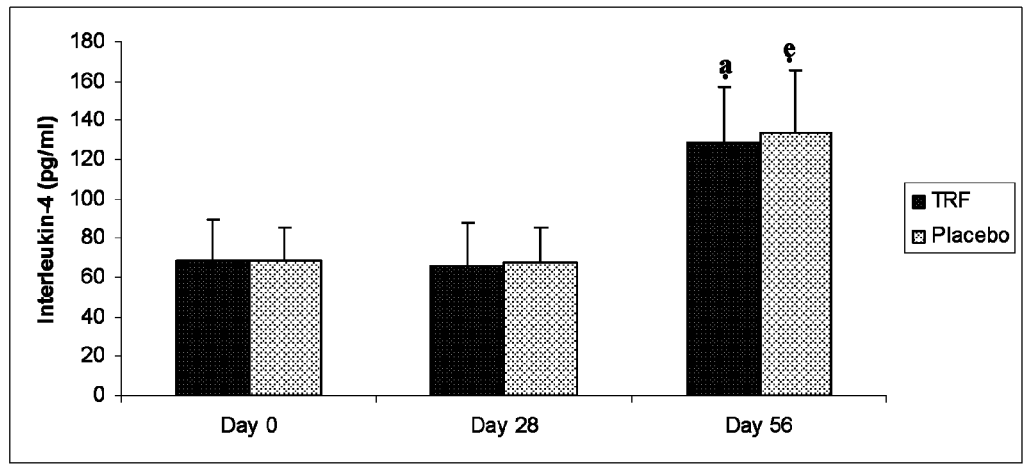
Figure-14: Effect of TRF supplementation on the production of IL-4 by Con A stimulated PBMC
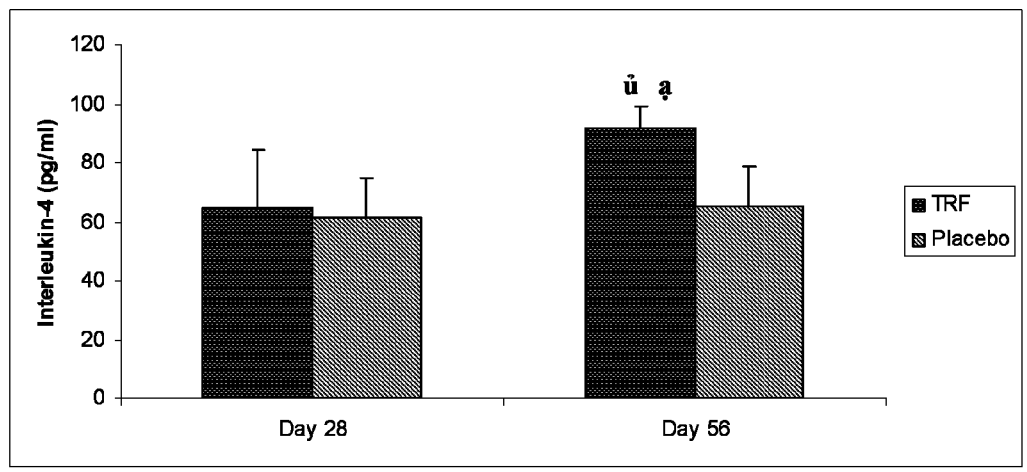
Figure-15: Effect of TRF supplementation on the production of IL-4 by TT stimulated PBMC

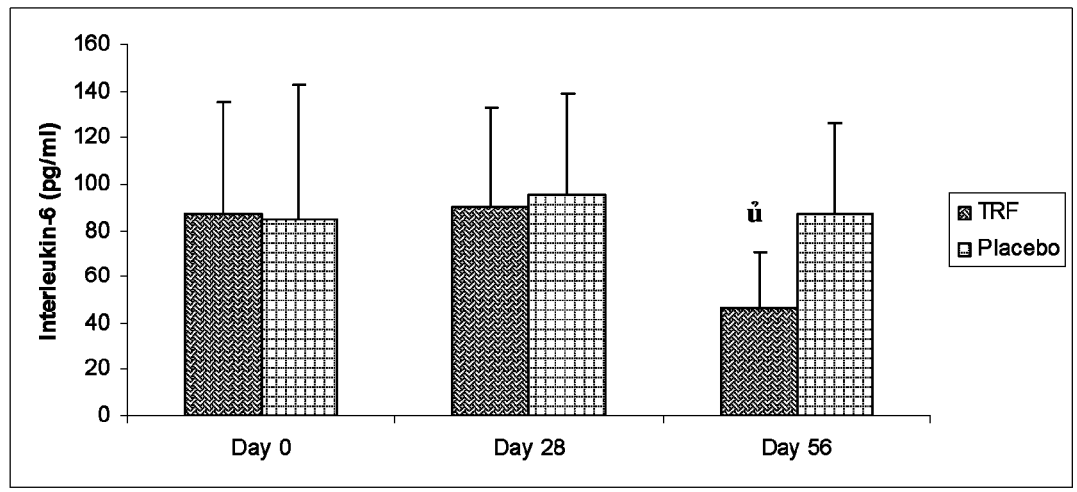
Figure-16: Effect of TRF supplementation on the production of IL-6 by LPS-stimulated PBMC
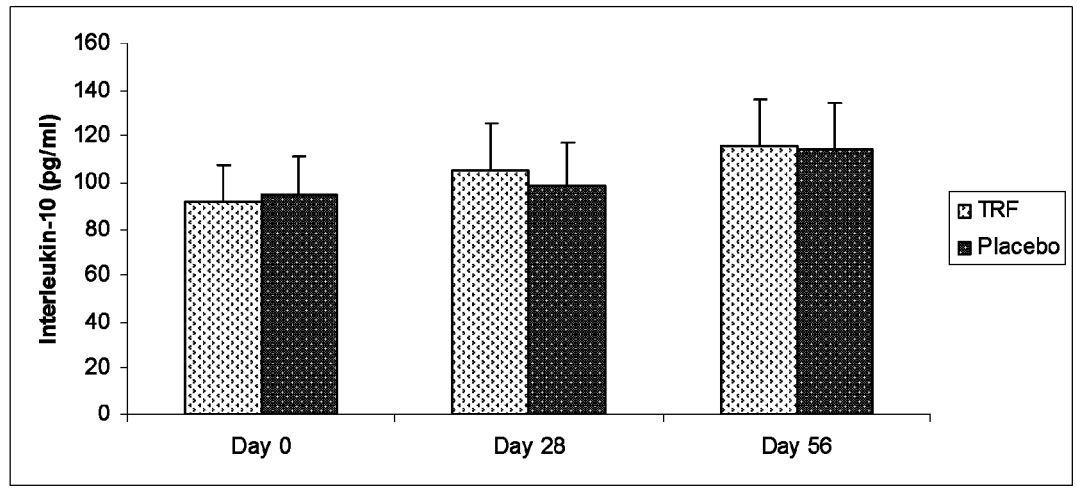
Figure-17: Effect of TRF supplementation on the production of IL-10 by Con A-stimulated PBMC

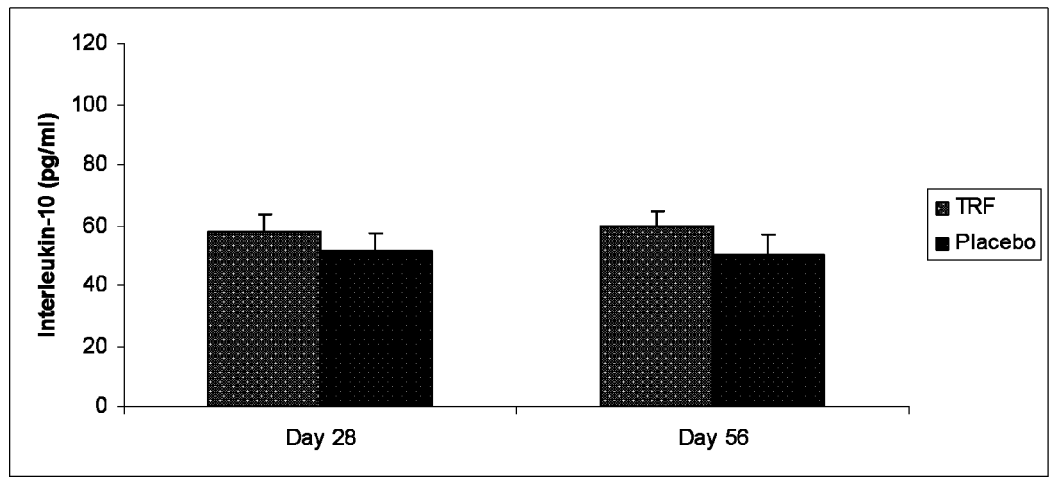
Figure-18: Effect of TRF supplementation on the production of IL-10 by TT-stimulated PBMC
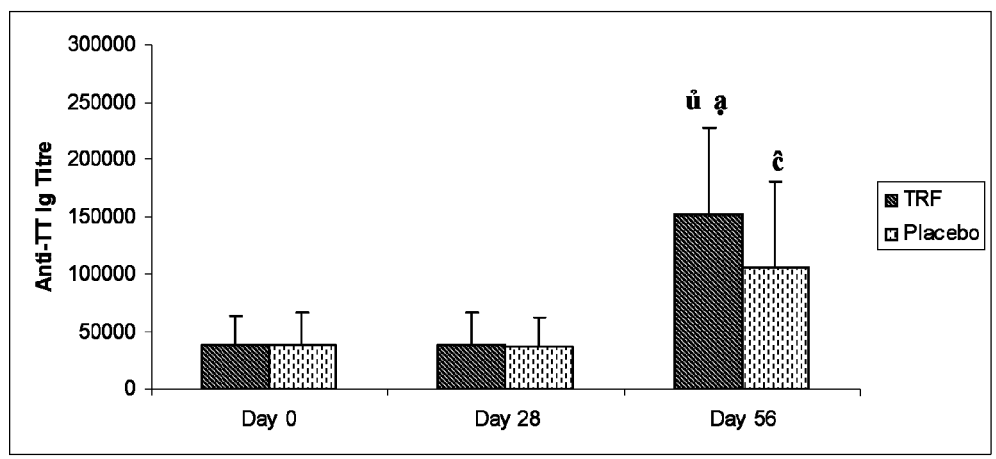
Figure-19: Histogram comparing the total Ig anti-TT titres between placebo- and TRF-supplemented volunteers

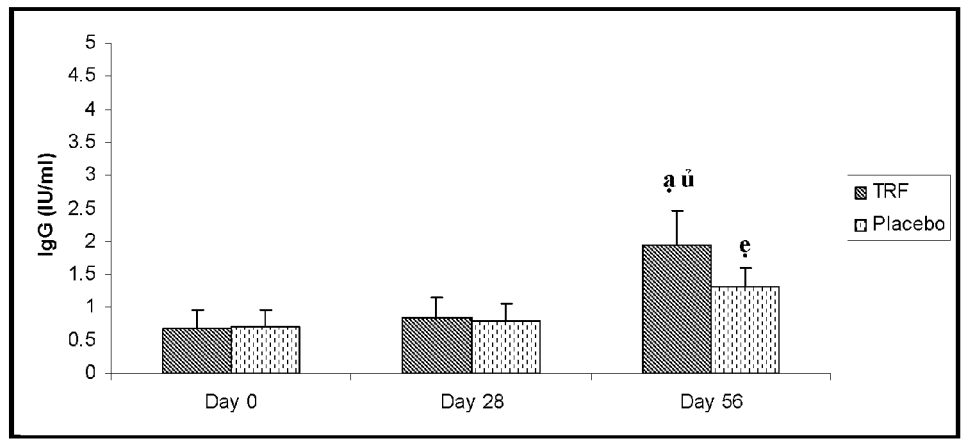
Figure-20: Histogram comparing the anti-TT IgG concentrations between placebo- and TRF-supplemented volunteers
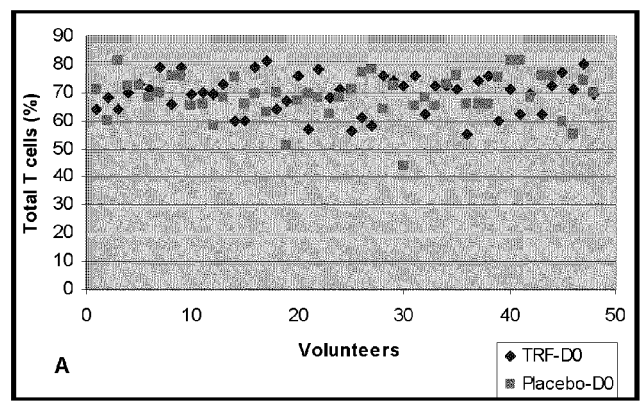
Figure 21: Scatter plots comparing the percentages of total T-lymphocytes between healthy volunteers supplemented with either TRF or placebo.

VITAMIN E SUPPLEMENTATION TO TETANUS TOXOID

FIELD OF INVENTION

The invention relates to a formulation for supplementation on immune response to a biological substance. More particularly, the formulation consists of one or more forms of Vitamin E which provides a supplementation on immune response to tetanus toxoid.

BACKGROUND OF THE INVENTION

Vitamin E is now considered a generic name describing bioactivities of both tocopherols and tocotrienols derivatives. Vitamin E is a fat soluble vitamin necessary in the diet of many species for normal reproduction, normal development of muscles, resistance of erythrocytes to hemolysis and various biochemical functions. The most broadly acknowledged function of Vitamin E, whereby it is an antioxidant. The Vitamin E content in crude palm oil ranges between 600-1000 parts per million (ppm) and is a mixture of tocopherols (18-22%) and tocotrienols (78-82%).

Vitamin E is the general name for a class of eight compounds: four isomers of tocopherol (alpha-tocopherol, beta-tocopherol, gamma-tocopherol, delta-tocopherol) and four isomers of tocotrienol (alpha-tocotrienol, beta-tocotrienol, gamma-tocotrienol, delta-tocotrienol). Structurally, tocopherols and tocotrienols share some resemblance consisting of common chromanol head and side chain at the C-2 position. Tocopherols and tocotrienols are sometimes collectively called tocols.

However, tocopherols and tocotrienols are distinguished by their side chains. Tocopherol has a saturated phytyl side chain; however tocotrienol possesses an unsaturated isoprenoid side chain. Tocopherols are found in vegetable oils such as those from canola, cotton seed, olive, peanut, sunflower, soybean and sunflower; especially seed oils. The major source of tocotrienols is plants oils and the richest sources are palm oil, rice bran oil, palm kernel oil and coconut oil.

Tocotrienols are also found cereal grains as oats, barley and rye. With the emergence of palm oil as the second largest edible oil in the world markets, technological advances have been made enabling the extraction of Tocotrienols from palm oil that is currently available commercially. Tocorienols in palm oil are many times potent as antioxidants than Tocopherols. Tocotrienols are also weekly absorbed by the skin and thus are well suited for use as Vitamin E cream.

Besides their function as antioxidant, Tocotrienol has been shown to have unique functional properties in contrast to Tocopherol. Tocotrienols have been shown to reduce plasma cholesterol levels, as well as other lipid and non-lipid related risk factors for cardiovascular diseases (Hood, 1996). It was also reported that tocotrienols possess anti-hypercholesterolemmic effects (Qureshi et al., 1991). The compound was also shown to display better anti-tumor activity than tocopherol (Carroll et al., 1996).Contrary to popular believe, Tocotrienol was observed in vitro to possess a remarkably higher antioxidant activity against lipid peroxidation than tocopherol (Serbinova et al., 1991) in biological systems. Tocotrienols that are largely found in palm oil are now commercially extracted as Enriched tocotrienols (ET).

Both Tocopherols and Tocotrienols are well recognized for their antioxidant effects and used in many topical preparations especially in cosmetics. The percentage of Tocopherols or Tocotrienols formulated into these topical preparations is very low and often below 0.1%.

Both Tocotrienols and Tocopherol are almost similar in structure and Tocopherols (Vitamin E) are present in topical preparations for many years. Therefore, the use of Tocotrienols at low concentration may not pose any risk of adverse cutaneous reactions.

Tetanus toxoid is a potent immunogen that induces long-lasting immunity in humans (Simonsen et al., 1986). Tetanus vaccination has had a dramatic impact on the incidence of tetanus infection in both adults and neonates worldwide. Vaccine-associated immunity to tetanus is associated with the production of neutralizing IgG antibodies to tetanus toxoid (Simonsen et al., 1986). Levels of these antibodies can be quantitated by using international standards and thus provide a useful model to investigate the protective efficacy of vaccine following tocotrienol supplementation.

Vitamin E is a major lipid-soluble anti-oxidant, which scavenges free radicals in biological membrane and protects the cellular structure against oxidative damage. Several studies have shown that vitamin E, both tocopherol and tocotrienol supplementation induces a favourable effect on animal and human immune system and has been implicated in the reduced risk for several immune and inflammatory diseases. The inventor's in the present invention had examined the immunomodulatory effects of orally administered tocotrienols and tocopherols in the mouse model upon an immunogenic challenge, and then investigated the effect of tocotrienol rich fraction (TRF) supplementation on immune modulation in normal healthy volunteers whose immune system was challenged with a booster tetanus toxoid (TT) vaccine.

The present has overcome the problem in the art by developing a supplementation on immune response to tetanus by using Vitamin E. The objective of the present invention discloses the effect of Vitamin E supplementation on immune modulation in a mammal, whereby the mammals are vaccinated with tetanus toxoid.

In addition, the present invention also relates on the effect of different types of Vitamin E such as tocotrienol rich fraction, delta tocotrienol and alpha-tocopherol supplementation on immune response to tetanus toxoid vaccination.

SUMMARY OF THE INVENTION

Accordingly, the object of the invention relates to a formulation for immune response supplementation in a biological active substance, said formulation comprising Vitamin E [preferably Tocotrienol Rich Fraction (TRF)]. The formulation is said of having the capability to be used as a supplement for immune response to tetanus toxoid vaccination. Further to that, the Tocotrienol Rich Fraction (TRF) is preferably selected from the group consisting of alpha-tocotrienol, delta-tocotrienol, gamma-tocotrienol and alpha-tocopherol.

Another aspect of the invention is directed the use of the formulation for the manufacture of a medication for supplementation on immune response, wherein the formulation is used for strengthening the immune response in a mammal.

In yet another embodiment of the present invention describes a method for strengthening the immune response in a person, wherein the method comprises administering to said person in need thereof an active amount of the formulation.

Furthermore, the invention relates to article of manufacture containing a packaging material contained within which is a formulation effective to activate the immune response to tetanus toxoid vaccination in a person and a packaging material comprises a label which indicates that the formulation can be used to strengthen the immune response and, wherein the formulation is preferably used as a pharmaceutical composition.

BRIEF DESCRIPTION OF THE DRAWINGS

FIG. 1 represents a flow diagram illustrates the participant allocation and retention throughout the study.

FIG. 2 represents concentrations of total vitamin E in the adipose tissue of mice supplemented with different isomers of vitamin E daily for 56 days.

FIG. 3 represents concentrations of α-tocopherol and tocotrienols in the adipose tissue of mice supplemented with different isomers of vitamin E daily for 56 days.

FIG. 4 represents histogram comparing the total Ig anti-TT titres between control and vitamin E supplemented mice FIG. 5 represents effect of vitamin E supplementation on mitogen- (Con A and LPS) and antigen-stimulated (TT) splenocyte proliferation in TT-immunised mice.

FIG. 6 represents effect of vitamin E supplementation on the production of IFN-γ by Con A- or TT-stimulated splenocytes.

FIG. 7 represents effect of vitamin E supplementation on the production of IL-4 by Con A- or TT-stimulated splenocytes.

FIG. 8 represents effect of vitamin E supplementation on the production of TNF-α by LPS-stimulated splenocytes FIG. 9 represents concentration of total vitamin E in the plasma of control and experimental volunteers FIG. 10 represents concentration of total alpha-tocopherol in the plasma of control and experimental volunteers.

FIG. 11 represents concentration of tocotrienols in the plasma of control and experimental volunteers.

FIG. 12 represents effect of TRF supplementation on the production of IFN-γ by Con A-stimulated PBMC FIG. 13 represents effect of TRF supplementation on the production of IFN-γ by TT-stimulated PBMC FIG. 14 represents effect of TRF supplementation on the production of IL-4 by Con A-stimulated PBMC.

FIG. 15 represents effect of TRF supplementation on the production of IL-4 by TT-stimulated PBMC.

FIG. 16 represents effect of TRF supplementation on the production of IL-6 by LPS-stimulated PBMC.

FIG. 17 represents effect of TRF supplementation on the production of IL-10 by Con A-stimulated PBMC.

FIG. 18 represents effect of TRF supplementation on the production of IL-10 by TT stimulated PBMC.

FIG. 19 represents histogram comparing the total Ig anti-TT titres between placebo- and TRF-supplemented volunteers.

FIG. 20 represents histogram comparing the anti-TT IgG concentrations between placebo- and TRF-supplemented volunteers.

FIG. 21 represents scatter plots comparing the percentages of total T-lymphocytes between healthy volunteers supplemented with either TRF or placebo.

DETAILED DESCRIPTION OF THE INVENTION

Definitions

Before describing the present invention in detail, it is to be understood that this invention is not limited to particular formulation types, manufacturing methods, or the like, as such may vary. It is also understood that the terminology used herein is for the purpose of describing particular embodiments only, and is not intended to be limiting.

The term "effective amount" of an active agent is meant a nontoxic but sufficient amount of an active agent to provide the desired beneficial effect. More particularly, by a "therapeutically effective" amount meant a non-toxic but sufficient amount of a beneficial agent to provide the desired therapeutic, or cosmeceutical effect.

The term "activation of the immune system" is meant improvements of all kinds of situations, where the immune system of a person is supposed to achieve a higher degree of performance including strengthening of the immune system of said person and reduction of the period The term "comprising" as used in this specification and claims means "consisting at least in part-of". Related terms such as comprise(s) and comprised are to be interpreted in similar manner.

The invention will now be described in more detail by reference to the following Figures and Examples. The following examples are provided for illustrative purposes only and are not intended to limit the invention.

(Best Mode For Carrying Out The Invention)

EXAMPLE 1

Vitamin E Supplementation for Mice

Concentrates of tocotrienol rich fraction (TRF), α-tocopherol (α-T) (Golden Hope Plantation, Malaysia) and δ-tocotrienol (δ-$T_3$) (Isei, Japan); 25 gauge gavage needle (Interfocus, England), soya bean oil (Mazola, Malaysia).

Blood Collection and Immunisation in Mice

Heparinised microhematocrit capillary tube (Fisher Scientific International, USA); 1.5 mL microcentrifuge tubes (Axygen, USA); heparin sodium salt (Sigma-Aldrich, USA); diethyl ether (Sigma-Aldrich, USA); alum-adsorbed tetanus toxoid vaccine (Biofarma, Bandung, Indonesia); 1 mL tuberculin syringe (Becton Dickinson, NJ, USA); 26 gauge sterile needles (Terumo Corp, Philippines).

Methyl Thiazole Tetrazolium (MTT) Assay

MTT kit (Chemicon, USA); 96-well flat-bottomed tissue culture plates (Nunc, USA); multichannel pipettor (LabMate, USA).

Physical Examination of Human Volunteers

Sphygmomanometer (Spirit, Taiwan); Littman® Stethoscope (3M, UK); Digital weighing scale (SECA, Hamburg, German).

Blood Collection from Human Volunteers 10 mL and 5 mL sterile syringes (Becton Dickinson, Singapore); 25, 23 and 21 gauge sterile needles (Terumo Corp, Philippines); cotton balls; tourniquet; sterile alcohol wipes (Becton Dickinson, NJ, USA); sterile Elastoplasts; disposable latex examination gloves (SE Sdn Bhd, Malaysia); 5 mL heparin tubes (Becton Dickinson, NJ, USA); sterile 5 mL Vacutainer Clot Activator tubes; 3 mL EDTA tubes, 3 mL Sodium Fluoride tubes (Becton Dickinson, NJ, USA); specimen bags and forms (supplied by PATHLAB).

Tetanus Toxoid Vaccination 1 mL sterile tuberculin needles (Becton Dickinson, Singapore); Tetanus toxoid (TT) Vaccines (Biofarma, Indonesia; Batch No. ATT073BA2006/2007).

Flow Cytometry 5 mL polystyrene round bottom tubes Falcon 2054 (Becton Dickinson, NJ, USA); FACS Lysing solution (Becton Dickinson, NJ, USA); TriTEST reagents such as TriTEST CD3 FITC/CD4 PE/CD45 PerCP, TriTEST CD3 FITC/CD8 PE/CD45 PerCP, TriTEST CD3 FITC/CD19 PE/CD45 PerCP and TriTEST CD3 FITC/CD16+CD56 PE/CD45 PerCP (Becton Dickinson, NJ, USA).

Lymphocytes Culture

RBC Lysis Buffer (eBioscience, USA); 15 mL and 50 mL polypropylene conical tubes Falcon 2097 (Greiner, USA); RPMI 1640 medium with L-glutamine (Gibco, Invitrogen Corp, New Zealand); Lyophilised Concanavalin A (Sigma-Aldrich Inc, Missouri, USA); Lyophilised Lipopolysaccharide (LPS) (Sigma-Aldrich Inc, Missouri, USA); Lyophilised tetanus toxoid (TT) (Calbiochem, Germany); 0.4% Trypan Blue Stain (Gibco, Invitrogen Corp, New Zealand); Penicillin-Streptomycin (Gibco, Invitrogen Corp, New Zealand); 10% Fetal Bovine Serum (FBS) (Gibco, Invitrogen Corp, New Zealand); 96-well flat-bottomed tissue culture plates (Nunc, USA); Neubauer Haemocytometer (Dynatech, Germany); Hand tally counter (Togoshi, Japan).

Enzyme Linked Immunosorbent Assay (ELISA)

96-well flat-bottomed NUNC™ high binding Immuno plates with Maxisorp™ surface (Nunc, USA); Phosphate buffered saline (PBS) tablets (Sigma-Aldrich Inc, Missouri, USA); Tween® 20 (MP Biomedicals Inc., Ohio, USA); ELISA kits for human IFN-γ, IL-4, IL-6 and IL-10 (eBioscience, CA, USA); ELISA kits for mouse IFN-γ, IL-4 and TNF-α (eBioscience, CA, USA); HRP-goat anti mouse IgG+A+M (H+L), HRP-goat anti human IgG (H+L) (Zymed-Invitrogen, CA, USA); 3,3',5,5'-tetramethylbenzidine (TMB) substrate (Becton Dickinson, NJ, USA); 2 M sulfuric acid (Sigma-Aldrich Inc, Missouri, USA); Human IgG Detection Kit (Immunobiological Laboratories, Hamburg, Germany).

HPLC Analysis

Hexane, ethanol, isopropyl alcohol and 0.9% sodium chloride (Molecular biology grade-Promega Corp, Wisconsin, USA); 15 ml polypropylene conical tubes Falcon 2097 (Greiner, USA).

Methods (Animal Study)

Vitamin E

Tocotrienol rich fraction (TRF) and α-tocopherol (α-T) concentrates were obtained from Golden Hope Plantation, Malaysia. Delta-tocotrienol (δ-$T_3$) was purchased from Isei, Japan. The purity of each isomer was approximately 97%. The proportion of TRF components includes α-tocopherol 32%, α-tocotrienol 25%, γ-tocotrienol 29% and δ-tocotrienol 14%. The concentrates of the isomers were then prepared as an emulsion with soya bean oil to give a final concentration of 20 mg/ml. Soya bean oil was used as the solvent for α-T, δ-$T_3$ and TRF concentrates because the oil is devoid of tocotrienols and it has low vitamin E activity as compared to other oils such as sunflower, safflower, and corn oil (Grela and Gunter, 1995). In this study, we were only able to compare the effects of TRF and δ-$T_3$ to the gold standard of vitamin E, α-T, because other pure forms of tocotrienols (i.e. α-$T_3$ and γ-$T_3$) were not available at the time of the study.

Mice

Female BALB/c mice (6 weeks of age) were purchased from Institute of Medical Research (Kuala Lumpur, Malaysia) and housed in the animal cabin of Malaysian Palm Oil Board (Bangi, Malaysia), under stable climatic and dietary conditions. Only young female BALB/c mice were used in this animal study because of the need to reduce the variations in immune responses which are known to be influenced by age, sex and strain of mouse (Shaikh et al., 1993). The female BALB/c strain was chosen simply for the reason that these animals are the most frequently used inbred strain of mice in animal studies (Iwata et al., 2007).

Study Design

Twenty (20) female BALB/c mice were divided into four groups of five mice each. Mice from each group were orally gavaged with 50 µL (1 mg) of TRF, α-T or δ-$T_3$ daily for two months. In this study, mice from the control group did not receive any supplements and were not gavaged with the soya bean oil vehicle. Based on the findings from our preliminary studies, short term (2 months) oral supplementation of soya bean oil did not change immune parameters as well as the total vitamin E accumulation in adipose tissue as compared to non-supplemented animals. This could be conceivably because soya bean oil had been shown to have low vitamin E activity (Grela and Gunter, 1995) and the animals were only gavaged with a very small amount of the oil (50 µL of soya bean oil) daily for a period of 8 weeks (2 months). Four additional naive mice which did not receive any supplements or vaccination were grouped as negative control and sacrificed on Day 0 to establish the baseline immune parameters prior to the start of the study. This study was approved by the Research and Ethics Committees of the International Medical University. Animal care and handling strictly followed the guidelines provided by the Ethics Committee of International Medical University.

Tetanus Toxoid Vaccination

All animals were immunised with 100 µL i.e. 4 Lf/mL of the alum-adsorbed tetanus toxoid (TT) vaccine (Biofarma, Indonesia) on day 14 (see Table-1). The TT vaccine was administered intramuscularly in the left hind leg quadriceps of each mouse. Booster doses of the TT vaccine were given on day 28 and day 42. All animals were primed with TT vaccine on day -14 and boosted twice at every two week interval following the standard immunisation regime for animal studies as reported by Gileadi et al. (2002). For all immunisations, mice were lightly anaesthetised with diethyl ether. Serum samples were obtained via retro-orbital bleeding on day 0 (baseline), day 28 (two-weeks after the first immunisation) and day 56 (two-weeks after the third immunisation). Upon completing the immunisations, all experimental animals were gavaged with the supplements for another two weeks before they were sacrificed on day 56. Blood, spleens and adipose tissues from the sacrificed animals were collected for various tests.

TABLE 1

Immunisation protocol of mice and study design

| Groups | TT Dose (Lf/100 µL) | Experimental Days | | | | |
|---|---|---|---|---|---|---|
| | | 0 | 14 | 28 | 42 | 56 |
| Control | 4 | a | TT | a TT | TT | a |
| α-T | 4 | a | TT | a TT | TT | a |
| δ-$T_3$ | 4 | a | TT | a TT | TT | a |
| TRF | 4 | a | TT | a TT | TT | a | a: serum samples were collected;
TT: TT vaccination; spleens and adipose tissues were removed from the animals on day 56.

Splenocyte Proliferation Assay

Spleen from the sacrificed mouse was removed aseptically into a petri dish containing culture medium (complete RPMI-1640 containing 5% (v/v) foetal bovine serum, 300 µg/mL L-glutamine and 100 IU/mL penicillin and 100 µg/mL streptomycin). Splenocytes were released from the spleen by gentle disruption of the splenic capsule. Following this, the splenocytes were gently teased out of the spleen. The splenic suspension was allowed to stand in room temperature for about one minute to allow clumps to settle to the bottom of the tube. Then the supernatant containing the single cell splenocyte suspension was transferred to a fresh tube. The splenocytes were recovered by centrifugation (1,200 rpm×10 min at 4° C.).

Splenic erythrocytes were lysed with lysis buffer (eBioscience, San Diego, Calif.) according to the protocol recommended by the manufacturers. The leucocytes were recovered once again by centrifugation (1,200 rpm×10 min at 4° C.). The leucocytes were then resuspended in complete RPMI-1640 medium. Cells were counted using a haemocytometer. Trypan blue dye exclusion technique was employed to facilitate exclusion of dead cells in the counting process. Following this, the splenocyte suspension was adjusted with culture medium to contain $1\times10^7$ cells/mL. The cell suspension was then divided into three tubes. To each of these tubes, either mitogen or specific antigen was added. The mitogens used were Concanavalin A (Con A) and lipopolysaccharide (LPS) at a concentration of 1 µg/mL each, whilst the specific antigen used was 10 µg/mL of pure tetanus toxoid (TT). One hundred microliters of these spleen cell suspensions were cultured in 96-well plates for 72 hours at 37° C. in a humidified, 5% $CO_2$ incubator. The proliferation of splenocytes was measured by MTT assay while the productions of cytokines by these cells were measured by ELISA.

Methyl Thiazole Tetrazolium (MTT) Assay

Proliferation of splenocytes was measured using the MTT assay (Hansen et al., 1989), which measures the reduction of 3-(4,5-dimethylthiazol-2-yl)-2,5-diphenyl tetrazolium bromide to formazan crystals. In this assay, the yellow MTT solution will be converted to a purple formazan product by the mitochondrial dehydrogenase of the viable cells. One-hundred microliters of splenocytes ($1\times10^7$ cells/mL) were seeded in triplicates in flat-bottomed 96-well plates and cultured in the presence or absence of 1 µg/mL Con A or LPS or 10 µg/mL TT. After 72 hours at 37° C. in 5% $CO_2$, the cells were incubated with 5 mg/mL MTT reagent for four-hours. The formazan precipitates were then dissolved by addition of 0.1 mL of HCl in isopropanol and mixed thoroughly by repeated pipetting. Cell proliferation was quantified using an ELISA reader at 570 nm.

Cytokine Analysis

After 72 hours of culture, supernatants from quadruplicate wells of the splenocytes culture were pooled into 1.5 mL microfuge tubes. The tubes were centrifuged (12,000 rpm×10 min at 4° C.) to remove cell debris. The culture supernatant was transferred to fresh sterile microfuge tubes and stored at −80° C. prior to analysis by ELISA. The concentration of various cytokines (IFN-γ, IL-4 and TNF-α) in cell-free culture supernatants were determined using commercial mouse cytokine ELISA kits according to the manufacturer's protocol (eBioscience, San Diego, Calif.). Briefly, sterile 96-well plates (Nunc, USA) were coated with 100 µL/well of the relevant capture antibody (e.g. anti-IFN-γ, anti-IL-4 or anti-TNF-α). The plates were sealed and incubated overnight at 4° C. Following this, the contents of the plates were discarded and the wells were washed thrice with wash buffer (PBS and 0.05% Tween-20). After the third wash, plates were inverted and blotted on absorbent paper to remove residual wash buffer. The wells were then blocked with 200 µL/well of assay diluent provided by the manufacturer. The plates were covered and incubated in the dark at room temperature for one-hour. After the incubation period, the blocking buffer was aspirated and the plates were washed as described previously. The supernatant from the splenocyte culture stored at −80° C. were thawed. Then 100 µL of this culture supernatant was added into the test wells as duplicate samples. The negative control wells contained 100 µL/well of assay diluent while the positive control consist of a titration of pure standard cytokine that was provided by the manufacturer. Samples of pure cytokines of known concentration were provided with each ELISA kit. One-hundred µL/well of top standard solutions of relevant cytokine (IFN-γ, IL-4 or TNF-α) were serially diluted using assay diluent. The plates were then covered and incubated for two hours at room temperature. Following this, the contents of the plates were discarded and the plates were washed.

Detection antibody and Avidin-horseradish peroxidase (HRP) reagent (provided by manufacturer) were diluted in assay diluent as recommended by the manufacturer. Then 100 µL of these solutions were added into all wells. Plates were covered and incubated for an hour in the dark. Following this, the contents of the plates were aspirated and the plates were washed seven times. During the last wash cycle, the wells were soaked in wash buffer for one minute before aspiration of the buffer. Then, 100 µL of the TMB substrate solution was added to all the 96-wells. The plates were incubated at room temperature for ten minutes to allow colour development and the reaction was stopped by adding 40 µL of 2M sulphuric acid to all the 96-wells. Absorbance was read at 450 ηm using an ELISA microplate reader.

The amount of cytokine produced was expressed as pg/mL and the detection limit of each of the cytokine ELISA kit was 8 pg/mL. The cytokine levels in negative control wells were mostly undetectable. Cytokine values in the negative control wells were subtracted from those in the experimental wells.

Determination of Serum Anti-TT Antibody Titres

Anti-TT antibodies in the mouse serum were detected and quantified by end-point titration using ELISA. Briefly, 96-well ELISA plates were coated with 100 µL/well of 3 µg/mL of TT solution in carbonate buffer (pH 9.2) and incubated overnight at 4° C. Subsequently, plates were washed three times using ELISA wash buffer (PBS with 0.05% Tween-20). After washing, the plates were blocked with 200 µL/well of ELISA blocking buffer (PBS with 1% (w/v) bovine serum albumin) for one hour at room temperature. Plates were then washed five times with wash buffer. Then 100 µL of the test samples were added as duplicates to this plate. The serum samples from animals supplemented with vitamin E and controls were serially diluted in blocking buffer using a two-fold serial dilution starting at 1:200 of the serum. Serum obtained from naive animals on day 0 served as the negative control for this assay. Plates were incubated at room temperature for two-hours.

After two-hours, the plates were washed five times and 100 µL of anti-mouse Ig conjugated with horseradish peroxidase (1:4000 dilution) was added to all the wells. Following a 60 minutes incubation at 37° C. and five washes, 100 µL of 3,3',5,5'-tetramethylbenzidine (TMB) substrate was added to all the wells. The colour was allowed to develop and the reaction was stopped by addition of 50 µL 2M sulfuric acid to all the wells. The absorbance 450 nm was read using an ELISA reader. The Ig titres were expressed as the reciprocal of the dilution giving an absorbance value ≤0.45 as described previously (Sneath et al., 1987).

Extraction of Vitamin E from the Mice Adipose Tissue

Approximately 0.5 g of mice adipose tissue was placed into a 15 mL centrifuge tube and homogenised with a mixture of hexane, ethanol and 0.9% sodium chloride (at the ratio of 4:1:1) at 10000 rpm for five minutes or until the tissue was reduced to a liquid form using a tissue homogeniser. The homogenate was then centrifuged at 2000 rpm for 10 minutes. The lipid-containing supernatant phase was transferred to 5 mL vials and dried down under nitrogen gas. The sample obtained was resuspended just before use in an appropriate amount of hexane (500 µl to 2 ml) for analysis by high performance liquid chromatography (HPLC).

HPLC Analysis

Analytical HPLC was performed using the LC-10AT HPLC system which consisted of a Shimadzu Model RF-10AXL fluorescence spectrophotometer, a column chamber and Shimadzu Class VP data acquisition software. The HPLC column was a YMC A-012, 5 µm, 150 mm×6 mm silica column. The excitation wavelength and emission wavelength of the fluorescence detector were set at 295 and 325 ηm, respectively. The mobile phase was hexane-isopropyl alcohol (99.5/0.5, v/v) with a flow rate of 2 mL/min. Sample injection volume was set at 10 µL and a standard solution mixture of α-tocopherols, α-, γ- and δ-tocotrienols was also injected accordingly into the system. The peak areas of the components in the sample were compared with those of the standards and were used for quantitative calculation.

Statistical Analysis

Data are presented as the mean±standard deviation (S.D.), where n is the number of mice used. In all experiments spleen cells were assessed individually (i.e. not pooled). Similarly, serum from each mouse was also tested individually. Either SPANOVA, one-way ANOVA, (followed by post hoc Tukey's pair wise comparisons) or Student's t-test was used to determine the significance between control and experimental animals (α-T, δ-T3 and TRF) with $P<0.05$ set as the level of acceptable statistically significant difference Methods (Clinical Study)

Trial Design

The clinical trial was approved by the Research and Ethics Committees of the International Medical University and followed the Malaysian guidelines for Good Clinical Practice (GCP). The study was a randomised, double-blinded, placebo-controlled trial. Volunteers were recruited from the $11^{th}$ Residential College, of the Engineering Faculty of Universiti Putra Malaysia (UPM). Volunteers were selected from this college because of their ideal age group (18-25 years.

In the animal study, all mice were subjected to three doses of tetanus toxoid immunization as the animals have not seen the tetanus antigen (i.e. no triple doses of TT vaccination) prior to the start of the study and as such they were given 3 doses of TT vaccine (each dose at every two week interval) as part of a standard vaccination regime.

Screening of Volunteers

After the general physical examination and history taking, 7 ml of blood was drawn from each volunteer and the samples were sent to an accredited medical laboratory (PATHLAB, Malaysia) for various biochemical tests such as fasting blood glucose levels, serum creatinine, total lipid profile including total cholesterol, high density lipoprotein (HDL) cholesterol, low density lipoprotein (LDL) cholesterol, triglycerides, total HDL ratio, liver function tests i.e. serum glutamic oxaloacetic transaminase (SGOT) and serum glutamic pyruvic transaminase (SGPT)) and total bilirubin. Blood was collected using a standard venepuncture technique (Nursing Standard, 1999; 2005) on days 0, 28 and 56 of the study. Urine samples were also obtained from the volunteers for pregnancy testing. Volunteers were asked to fast 10 to 12 hours the night before their blood was taken for these biochemical tests.

The same biochemical parameters were measured again at the end of the trial (Day 56) primarily to ensure that the kidney and liver functions are normal in all volunteers after the supplementation.

Recruitment of Volunteers

Selected volunteers were randomly assigned to receive either placebo (control group) or 400 mg of TRF (study group) supplementation daily. The block randomization scheme was used in the study.

All 108 study participants were equally allocated in a 1:1 ratio to a bottle filled with either TRF or placebo capsules. Two identical bottles, labeled number 1 and number 2, were used throughout the study. For each participant, the researchers chose one of the two bottles in an alternating manner (i.e. the first participant received bottle 1, the second participant received bottle 2, etc.) and recorded the chosen bottle number in the study participant's file. During the period of carrying out the invention, volunteers were given three meals a day with a standard recommended diet schedule in order to keep the calorie intake constant amongst the volunteers and to minimise the effects of diet on the overall absorption of vitamin E. On weekdays, the participants had breakfast on site and took their afternoon meals with them. Dinner was served in the college cafeteria daily. All meals were prepared in the cafeteria of the college.

During the initial one month period, six volunteers in the treatment group and two volunteers from the placebo group withdrew from the trial. All volunteers had blood drawn at baseline (Day 0), Day 28 and 56. Compliance was checked by pill counts at each visit. FIG. 1 represents participant's allocation and retention throughout the invention.

At the end of the trial, data gathered from the analysis of blood samples from each volunteer were computed into a database (Microsoft Excel®, 2003) and statistical analyses were performed using the SPSS for Windows (version 11.0; SPSS Inc., Chicago, Ill.).

Supplements

The TRF supplements used in this study were Tocovid SupraBio manufactured by Hovid Sdn Bhd (Ipoh, Malaysia). The composition of Tocovid soft gel capsules includes a mixture of tocotrienols and α-tocopherols (see Table-2). The mixed tocotrienols (TRF) capsule each contain 200 mg of the supplement while the placebo capsules were made of palm olein (cooking oil) which were totally devoid of vitamin E.

TABLE 2

Tocotrienol and tocopherol composition of TRF supplements

| Vitamin E | Composition |
| --- | --- |
| d-Alpha-Tocotrienol | 61.52 mg |
| d-Gamma-Tocotrienol | 112.80 mg |
| d-Delta-Tocotrienol | 25.68 mg |
| d-Alpha-Tocopherol | 91.60 IU |
| Plant Squalene | 51.28 mg |
| Phytosterol Complex | 20.48 mg |
| Phytocarotenoid Complex | 0.36 mg |

(adapted from http://www.hovid.com/cn/index/products/p_dietary.html, 2006)

Administration of Supplements

Volunteers were asked to start taking their daily supplements of vitamin E or placebo on Day 0 of this study for 8-weeks. They were instructed to take two capsules daily preferably with lunch or dinner to facilitate compliance. The oral intake of the supplements for the study group was 400 mg of mixed tocotrienols daily.

Tetanus Toxoid (TT) Vaccination

The TT vaccine (Biofarma, batch No. ATT073BA2006/2007) was administered via intra-muscular injection into the deltoid muscle of the non-dominant arm by a registered nurse. The dose used was 20 flocculation units (Lf) of TT vaccine in a final volume of 0.5 mL. No vaccine-related serious adverse event occurred during the immunisation period and the course of the study.

Collection of Blood Samples

Blood samples were drawn from healthy volunteers by a registered nurse or doctor on the screening day as well as on days 0, 28 and 56. A butterfly or 10 mL plastic syringe connected to a vacuum tube holder was used for venipuncture. Blood samples were collected into different types of blood collection tubes based on the test that was to be carried out on the blood samples, and the tubes were filled to capacity. After blood collection, the tubes were inverted three times to ensure proper mixing of the blood with clot activators or anticoagulants. The types of blood collection tubes used in this study are described in Table-3. All the blood collection tubes were used before their expiration dates.

TABLE 3

Tubes Used for Blood Collection

| Types of Blood Collection Tubes | Pre-Screening | Day 0 | Day 28 | Day 56 |
|---|---|---|---|---|
| Clot Activator tube (5 ml) | 1 tube | — | — | 1 tube |
| EDTA tube (3 ml) | 1 tube | — | — | 1 tube |
| Sodium Fluoride tube (3 ml) | 1 tube | — | — | 1 tube |
| Heparinised tube (5 ml) | — | 2 tubes | 2 tubes | 2 tubes |

Isolation of Peripheral Blood Leucocytes

Peripheral blood leucocytes (PBL) were isolated from heparinised blood obtained from healthy volunteers using the red blood cell (RBC) lysis technique. From the optimisation studies conducted previously, it was determined that leucocytes from 1 mL of blood were sufficient for the proliferation and cytokine assays that will be performed for this study. Approximately 1 mL of heparinised blood collected from the volunteers was aliquoted into appropriately labelled 15 mL conical tubes. About 3 mL of RBC lysis buffer was then added into each of the tube that contains the blood sample. The tubes were capped and inverted four times until the mixture became homogenous and incubated at room temperature for 3 minutes to allow the RBC lysis reaction to take place. The reaction was stopped by the addition of ice-cold PBS and the tubes were centrifuged at 4000 rpm for 10 minutes at 4° C. After centrifugation, the upper clear red supernatant was discarded and the cells were washed once in ice-cold PBS.

The centrifugation step was repeated and the pellet containing leucocytes was resuspended in 5 mL of complete RPMI-1640 containing 5% (v/v) of FBS, 1% of penicillin, streptomycin and L-glutamine. The tubes were gently tapped to loosen the cells from the bottom of the tubes and the tubes were inverted gently to allow the formation of a cell suspension. The tubes were kept on ice and cell count was performed using a haemocytometer. Blood leucocytes cultures were carried out on Days 0, 28 and 56.

Counting and Proliferation of Peripheral Blood Leucocytes

Counting of viable blood leucocytes was performed individually for all samples using a haemocytometer. Trypan Blue exclusion method was used to identify the dead cells. A 10× dilution of the leucocytes suspension was made in a sterile 1.5 mL Eppendorf tubes by adding 100 µL of cell suspension into 900 µL of complete RPMI. Then 40 µL of Trypan Blue dye (0.4%) was added to the tube and the solution was mixed by inverting the tube several times. Approximately 10 µL of cell suspension was pipetted into the counting chamber of a haemocytometer slide and the number of non-stained, viable cells was counted. The number of viable leucocytes was calculated and the volume of the cell suspension was adjusted with culture medium (RPMI 1640) to obtain a final cell concentration of $1 \times 10^7$ cells/mL. Leucocytes were seeded in a 96-well plate at $1 \times 10^6$ cells/well and these cells were stimulated individually with either 1 µg/mL of Con A or LPS or 10 µg/mL of TT. Cells were cultured for 72 hours at 37° C. in a humidified atmosphere of 5% $CO_2$. The peripheral blood leucocyte cultures were harvested after three days.

ELISA

After 72 hours culture, supernatant from the wells of the peripheral blood leucocyte culture were pooled into 1.5 mL microfuge tubes. The tubes were centrifuged (12,000 rpm×10 min at 4° C.) to remove cell debris. The culture supernatant was transferred to fresh sterile microfuge tubes and stored at −80° C. prior to ELISA. Estimations of IFN-γ, IL-4, IL-6 and IL-10 from culture supernatant of human PBLs were performed using commercial ELISA kits (eBioscience, San Diego, Calif.) according to the manufacturer's instructions. Limit of sensitivity for detection of IFN-γ and IL-6 was 8 pg/mL and 1 pg/mL, respectively. Detection limit for both IL-4 and IL-10 was 4 pg/mL. Total Anti-TT Ig titers in plasma collected on day 0, 28 and 56 were also determined using ELISA. Blood samples was collected in heparinised tube were spun at 2000 rpm for 10 minutes at room temperature. The plasma was isolated from the sedimented red blood cells and transferred into a sterile 1.5 mL centrifuge tube. Plasma samples were serially diluted in assay diluent using a twofold serial dilution starting at 1:400. Sera obtained from unimmunized volunteers served as the negative control for serum total Ig titration.

After two hours incubation of the plasma samples, ELISA plates were washed and HRP conjugated with goat-anti-human Ig were added at a dilution of 1:5000. Following 60 minutes of incubation and five washes, 100 µL of TMB substrate was added and as the color developed, the reaction was stopped by addition of 2 M sulphuric acid (50 µL/well). Plates were read at 450 ηm using an ELISA reader and total Ig titers were expressed as the reciprocal of the dilution giving an absorbance value ≤0.45.

Plasma samples with the known Ig titers were then assayed to quantify the concentration of IgG (IU/mL) in the samples using the Anti-Tetanus Human IgG ELISA kit (IBL, Hamburg). The IgG microwell plates were coated with inactivated tetanus toxoid antigen. Manufacturer's calibrators (concentration ranging from 5-40 IU/mL) and negative controls were run in duplicate for each plate. Concentrations of IgG in samples were calculated using the standard curve of the calibrator.

Blood Leucocytes Staining

Approximately 1 mL of blood drawn from volunteers on Days 0, 28 and 56 were collected into sterile $K_3$ EDTA VACUTAINER® blood collection tubes for flow cytometry analysis. Four different types of TriTEST reagents (see Table 4), namely CD4, CD8, CD19, CD16+CD56 antibodies (Becton Dickinson, NJ, USA) were used to stain the blood samples following the method recommended by the manufacturer. All four antibodies contain immunofluorescence reagents specifically fluorescein isothiocyanate (FITC)-labelled CD3 and peridinin chlorophyll protein (PerCP)-labelled CD45 antibodies. The CD3 antibody identifies mature human T-lymphocytes ($CD3^+$) and T-cell antigen receptor (TCR) complex (Brenner et al., 1986) while the CD45 antibody recognises human leukocytes antigen (HLA) (Schmidt, 1989). Four round-bottom sterile Falcon tubes were prepared for each blood sample. Twenty µL of different TriTEST reagents were then pipetted into bottom of the respective tubes (see Table-4). Following this, 50 µL of well mixed, anticoagulated whole blood was pipetted into the bottom of all four tubes for each blood sample.

Tubes were capped and gently tapped at the bottom to thoroughly mix the antibodies with the blood cells. The tubes were then incubated in the dark for 15 minutes at room temperature. The incubation was performed at room temperature to decrease variations in leucocyte surface antigen expression that was reported to occur when samples were subjected to cool-warm temperature changes (Forsyth and Levinsky, 1990; (Repo et al., 1995). After the incubation, 450 µL 1× FACS lysing solution was added into each tube. The tubes were capped and gently tapped at the bottom to ensure mixing.

The tubes were incubated for another 15 minutes in the dark. Following this, the samples were immediately analysed using flow cytometer.

TABLE 4

TriTEST reagents (antibodies) used in flow cytometry analysis

| Tube | TriTEST Reagent (Becton Dickinson, NJ, USA) | Leucocytes Detected |
|---|---|---|
| 1 | CD3/CD4/CD45 | $CD4^+$ T-lymphocytes |
| 2 | CD3/CD8/CD45 | $CD8^+$ T-lymphocytes |
| 3 | CD3/CD19/CD45 | B-lymphocytes |
| 4 | CD3/CD16 + CD56/CD45 | Natural killer (NK) cells |

Flow Cytometry Analysis

Data from the Tri-test antibody-stained samples was acquired by flow cytometry (FACS Calibur, Becton Dickinson, San Jose, Calif.) using the Multiset software provided by the manufacturer. Calibration of the flow cytometer was performed daily prior to each run using Calibrite Beads provided by the manufacturer. The parameters measured using the Multiset software include numbers and percentages of T-lymphocytes, T-helper cells, $CD8^+$ T-lymphocytes, B-lymphocytes, NK-cells, as well as the CD4:CD8 T-cell ratio.

Vitamin E Extraction from Blood Plasma and HPLC Analysis

Blood samples collected in heparinised tube were spun at 2000 rpm for 10 minutes at room temperature. The plasma was isolated from the sedimented red blood cells and transferred into a sterile 1.5 mL centrifuge tube. Following this, 500 µL of the plasma was then added to a tube containing 0.5 mL of 0.5% NaCl, and ethanol. Then, 400 µL of hexane was added into each tube.

The mixture was shaken vigorously for an hour using a minishaker. The tube was then spun at 3000 rpm for 10 minutes at room temperature. After centrifugation, the clear hexane phase was transferred carefully into a clean vial and blow-dried under nitrogen gas. An aliquot of the lipid sample was reconstituted in 500 µL hexane. Then 10 µL of the solution was injected into a HPLC system.

Statistical Analysis

Data obtained from the study were processed using SPSS for Windows (Version 10.0; SPSS Inc., Chicago, Ill.). Either Split Plot ANOVA (SPANOVA) or One-Way ANOVA was used to determine the significance between the control (placebo) and experimental (TRF) groups at three different time points i.e. Day 0, 28 and 56. Data are presented as the mean±S.D.

Results (Animal Study)

Vitamin E Levels in Adipose Tissues of Mice

Animals in the experimental groups fed with different isomers of vitamin E primarily $\alpha$-T, TRF and $\delta$-$T_3$ showed significant ($P<0.05$) levels of total vitamin E accumulation in adipose tissues compared to the unsupplemented control mice (see FIG. 2). The total vitamin E levels were highest in adipose tissues of animals fed with $\delta$-$T_3$ followed by TRF and $\alpha$-T. In mice supplemented with different types vitamin E, the $\alpha$-T and alpha-tocotrienol ($\alpha$-$T_3$) isomers was present in the adipose tissue of all the animals. However, when compared to the rest of the animal groups, the $\alpha$-T fed animals had significantly ($P<0.05$) high concentrations of tocopherol and likewise TRF gavaged animals showed highly significant ($P<0.01$) amounts of $\alpha$-$T_3$ accumulated in their adipose tissues (see FIG. 3). The concentrations of $\delta$-T3 in adipose tissue were highest in the $\delta$-$T_3$ fed animals and the levels were highly significant ($P<0.01$) compared to the rest of the groups (see FIG. 3). The adipose tissues of control and $\alpha$-T supplemented animals did not have any detectable amounts of $\delta$-$T_3$ or $\gamma$-$T_3$. Only the TRF supplemented animals showed the presence of all four isomers in the adipose tissue and the concentrations of gamma-tocotrienol ($\gamma$-$T_3$) was highly significant ($P<0.01$) in this group compared to the rest of the animals. Experimental groups were fed with 1 mg of different isoforms of vitamin E i.e. TRF, $\alpha$-T or $\delta$-$T_3$.

Control mice were not supplemented with any isomers of vitamin E. Significant differences between control and experimental groups were designated as $^eP<0.05$ (ANOVA).

Significant differences between $\alpha$-T fed mice and the rest of groups were designated as $^eP<0.01$ (ANOVA) for $\alpha$-T concentration in adipose tissue. As for $\delta$-$T_3$ concentration in adipose tissue, differences between $\delta$-$T_3$ fed mice and animals from the control, $\alpha$-T and TRF groups were designated as $^eP<0.01$ (ANOVA). Accumulation of $\alpha$-$T_3$ and $\gamma$-$T_3$ in adipose tissue showed significant differences in TRF supplemented mice as compared to the animals from the control, $\alpha$-T and $\delta$-$T_3$ groups and were designated as $^eP<0.01$ (ANOVA) and $^gP<0.01$ (ANOVA) respectively.

Production of Anti-Tetanus Toxoid Antibody in Mice Supplemented with Vitamin E

The BALB/c mice were divided into four groups i.e. three experimental groups and one control group. The mice from the experimental group were orally gavaged with different types of vitamin E. All animals received three doses of tetanus toxoid (TT) vaccines. The TT-specific antibody titres in the serum of control and experimental animals were measured on day 0 (baseline), day 28 and day 56 using ELISA. As shown in FIG. 4, the anti-TT Ig titres in TT-immunised mice was significantly ($P<0.05$) enhanced following daily supplementation of vitamin E i.e. $\delta$-T3, $\alpha$-T or TRF. The augmentation of the anti-TT Ig titres was statistically significant ($P<0.05$) in all vitamin E supplemented groups after the first vaccination on day 28 as compared to the control animals. However, the enhancement of the anti-TT titres was not significantly different amongst the experimental group after the first vaccination (see FIG. 4). Following the third TT vaccination, mice gavaged with different isomers of vitamin E for 56 days had significantly ($P<0.05$) higher anti-TT antibody titres as compared to untreated mice (see FIG. 4).

As shown in FIG. 4, mice supplemented with the $\delta$-$T_3$ isomer had the highest anti-TT antibody titres after the third vaccination. This was followed by TRF and $\alpha$-T fed mice. Anti-TT antibody titres in mice supplemented with $\delta$-$T_3$ and TRF was significantly ($P<0.01$) higher than in the $\alpha$-T treated mice.

In addition, TRF and $\delta$-$T_3$ fed mice also showed highly significant ($P<0.01$) antibody titres after the third immunisation as compared to first immunisation. The baseline (day 0) titres of serum anti-TT antibodies were low in all animals and were almost identical in control and experimental groups (see FIG. 4) indicating that the immune state in the animals were similar at the start of the study. These findings indicate that tocotrienols, primarily $\delta$-$T_3$ and TRF, significantly enhanced the production of anti-TT antibody in TT vaccinated mice.

Significant differences between control and experimental groups on day 28 and 56 were designated as $^aP <0.05$ (SPANOVA) and $^eP <0.05$ (SPANOVA) respectively. Significant differences between $\delta$-$T_3$ and $\alpha$-T fed animals on day 56 were designated as $^bP <0.01$ (ANOVA); while the differences between TRF and $\alpha$-T supplemented groups on day 56 were designated as $^cP <0.01$ (ANOVA). Significant differences between day 56 and day 28 in TRF and $\delta$-$T_3$ fed animals were designated as $^fP <0.01$ (SPANOVA).

Proliferation of Splenocytes from TT-Vaccinated Mice Supplemented with Vitamin E The BALB/c mice were divided into four groups i.e. three experimental groups and a control group. The mice from the experimental group were orally gavaged with different isomers of vitamin E. All animals received three doses of tetanus toxoid (TT) vaccines. On Day 56, spleens from sacrificed mice were removed and cultured in the presence of Con A, LPS or pure TT.

FIG. 5 shows the effect of supplementation of different isomers of vitamin E on mitogen or antigen-induced proliferation of splenocytes from control and vitamin E supplemented mice. Splenocytes from TT immunised mice supplemented with either $\delta$-$T_3$, TRF or $\alpha$-T showed a significantly ($P<0.05$) greater proliferative response to Con A (1 µg/mL) or TT (10 µg/mL) compared to control mice (see FIG. 5). Cell proliferation was slightly increased in $\delta$-$T_3$ supplemented group and this was followed by TRF and $\alpha$-T supplemented groups. However, there was no significant ($P>0.05$) differences in splenocyte proliferation between the vitamin E treated groups following Con A or TT stimulation. In addition, LPS (1 µg/mL) did not induce significant ($P>0.05$) splenocyte proliferation in the vitamin E treated groups as compared to the control group. These results indicate that both tocotrienol and tocopherol supplementation can augment proliferation of Con A- or TT-stimulated murine splenocytes. Groups of five female mice were immunised with TT vaccine (4 Lf/mL) on days 14, 28 and 42. Mice were sacrificed two-weeks (day 56) after the last vaccination.

Significant differences between the control and experimental groups in Con A stimulated cultures were designated as $^aP <0.0$ (ANOVA); while those between the control and experimental groups in TT stimulated cultures were designated as $^eP <0.05$ (ANOVA). Following LPS stimulation, no significant differences in splenocyte proliferation were observed between both control and experimental groups (ANOVA).

Effect of Vitamin E Supplementation on the Production of Cytokines by Mitogen or Antigen Stimulated Splenocytes from TT Immunised Mice The BALB/c mice were divided into four groups i.e. three experimental groups and one control group. The mice from the experimental groups were orally gavaged with different isomers of vitamin E. All animals received three doses of tetanus toxoid (TT) vaccines. The control and experimental mice were sacrificed on Day 56. The spleens from sacrificed mice were removed and cultured in the presence of Con A or pure TT. The culture supernatant was harvested following 72 hours of culture and the amount of cytokines (IFN-$\gamma$, IL-4 and TNF-$\alpha$) produced was quantified using ELISA.

Effect of Vitamin E Supplementation on the Production of IFN-$\gamma$ by Con A or TT Stimulated Splenocytes As shown in FIG. 6, the concentrations of IFN-$\gamma$ from Con A-stimulated splenocytes harvested from TT vaccinated mice fed with different isomers of vitamin E were significantly ($P<0.05$) higher than those of control mice. Compared to the $\alpha$-T treated mice, animals supplemented with $\delta$-$T_3$ showed significant ($P<0.05$) increase in the cytokine production following Con A stimulation. However, no significant difference in the levels of IFN-$\gamma$ was observed between the $\alpha$-T and TRF fed mice.

In TT-stimulated splenocytes, the IFN-$\gamma$ levels were significantly augmented in all vitamin E supplemented groups as compared to control animals (see FIG. 6). Within the treated groups, however, the cytokine levels were not significantly different. In addition, splenocytes from naive (untreated mice and non-vaccinated) mice stimulated with Con A produced relatively low amounts of IFN-$\gamma$ as compared to control animals.

Effect of Vitamin E Supplementation on the Production of IL-4 by Con A or TT Stimulated Splenocytes FIG. 7 shows the production of IL-4 by splenocytes from control and vitamin E treated mice following three doses of TT vaccination. As compared to the control mice, Vitamin E treated animals showed significant ($P<0.05$) enhancement in the IL-4 production in both Con A and TT-induced proliferation of splenocytes. However, there was no significant difference observed in the levels of IL-4 amongst the vitamin E supplemented groups. Splenocytes from naive animals (untreated mice and non-vaccinated) produced relatively very low amounts of IL-4 as compared to control animals.

Effect of Vitamin E Supplementation on the Production of TNF-$\alpha$ by LPS Stimulated Splenocytes LPS-induced TNF-$\alpha$ production was found to be significantly ($P<0.05$) reduced in mice supplemented with different isomers of vitamin E and vaccinated with TT (see FIG. 8). The production of TNF-$\alpha$ were almost identical in all Vitamin E treated animals and no differences were observed between these groups. Groups of five female mice were immunised with TT vaccine (4 Lf/mL) on days 14, 28 and 42. Mice were sacrificed on day 56, two weeks after the last vaccination. Splenocytes were prepared from the spleen of the sacrificed mice and cultured in the presence of Con A (1 µg/mL) or TT (10 µg/mL). Results are expressed as concentration (pg/mL).

The culture supernatant was harvested following 72 hours of culture and the amount of IFN-$\gamma$ produced was quantified using ELISA. Significant differences between the control and experimental animals in Con A stimulated splenocytes were designated as $^aP <0.05$ (ANOVA); while the difference between control and experimental group in TT stimulated splenocytes were designated as $^eP <0.05$ (ANOVA). The differences between $\delta$-$T_3$ and $\alpha$-T supplemented animals in Con A stimulated splenocytes were designated as $^bP <0.05$ (Student's T-test). No differences were observed between TRF and $\alpha$-T supplemented animals in Con A stimulated splenocytes. Significant difference between the naive and control animals in Con A stimulated splenocytes were designated as $^sP <0.05$ (Student's T-test). Groups of five female mice were immunised with TT vaccine (4 Lf/mL) on days 14, 28 and 42. Mice were sacrificed two-weeks (day 56) after the last vaccination. Splenocytes were prepared from the spleen of the sacrificed mice and cultured in the presence of Con A (1 µg/mL) or TT (10 µg/mL). Results are expressed as concentration (pg/mL). The culture supernatant was harvested following 72 hours of culture and the amount of IL-4 produced was quantified using ELISA Significant differences between control and experimental group in Con A stimulated splenocytes were designated as $^sP <0.05$ (ANOVA); while the difference between control and experimental group in TT stimulated cultures were designated as $^eP <0.05$ (ANOVA). Significant difference between the naive and control animals in Con A stimulated splenocytes were designated as $^sP <0.05$ (Student's T-test). Groups of five female mice were immunised with TT vaccine (4 Lf/mL) on days 14, 28 and 42. Mice were sacrificed two-weeks (day 56) after the last vaccination. Splenocytes were prepared from the spleen of the sacrificed mice and cultured for 72 hours in the presence of LPS (1 µg/mL). Results are expressed as concentration (pg/mL). The culture supernatant was harvested following 72 hours of culture and the amount of TNF-α produced was quantified using ELISA. Significant differences between control and experimental group were designated as $^a$P <0.05 in the LPS stimulated splenocytes (ANOVA).

High Levels of Vitamin E in Plasma of Volunteers Supplemented with TRF

Plasma samples obtained from volunteers were analysed using HPLC to quantify the concentrations of total tocopherols and tocotrienols. As shown in FIG. 9, plasma concentrations of total vitamin E (tocopherols and tocotrienols) increased significantly (P<0.05) after four- (day 28) and eight-weeks (day 56) of TRF supplementation in the experimental group. In contrast, the total vitamin E concentration in the plasma of the placebo group remained constant at both time points (see FIG. 9). However, the differences of total vitamin E levels in plasma of TRF-supplemented group between day 28 and 56 were not statistically significant (see FIG. 9) suggesting, perhaps, that the body elimination process is effective in sustaining some optimal levels of vitamin E.

The amount of endogenous α-tocopherol in the blood of healthy volunteers increased significantly (P<0.05) on days 28 and 56 as compared to day 0 (see FIG. 10). The α-tocopherol concentration was significantly (P<0.05) augmented in TRF-supplemented group as compared to the placebo group on days 28 and 56. Mean plasma α-, γ- and δ-tocotrienol concentrations also increased significantly (P<0.01 and P<0.05) in volunteers who received TRF as compared to placebo on days 28 and 56 (see FIG. 11). Amongst the concentration of tocotrienol isomers in the TRF supplemented group on days 28 and 56, the α-tocotrienol was the highest and this was followed by γ- and δ-tocotrienol (see FIG. 11). The concentrations of tocotrienols in the placebo group on days 28 and 56 remained the same and the amounts did not differ significantly (P>0.05) as compared to day 0. One hundred volunteers were randomly assigned in two groups i.e. control (received placebo) or experimental (received 400 mg TRF daily). Blood was drawn from both grous on day 0, day 28 and day 56.

Plasma was isolated from the blood for HPLC analysis as described in the methods section. The plasma concentration of total vitamin E from this analysis is reported in µg/mL.

Significant difference in plasma vitamin E levels between control and experimental group on day 28 is designated as $^a$P <0.05 (ANOVA). Significant difference in plasma vitamin E levels between control and experimental group on day 56 is shown as $^y$P <0.05 (ANOVA). Significant differences in plasma vitamin E levels between experimental groups on day 0 and day 28 are designated as $^a$P <0.05 (SPANOVA). Significant differences in plasma vitamin E levels between experimental groups on day 0 and day 56 are designated as $^e$P <0. 05 (SPANOVA).

One hundred volunteers were randomly assigned in two groups i.e. control (received placebo) or experimental (received 400 mg TRF daily). Blood was drawn from both groups on day 0, day 28 and day 56. Plasma was isolated from the blood for HPLC analysis as described in the methods section. The plasma concentration of alpha-tocopherol from this analysis is reported in µg/mL.

Significant difference in plasma α-tocopherol concentration between control and experimental group on day 28 is shown as $^a$P <0.05 (ANOVA) while difference between control and experimental group on day 56 is shown as $^e$P <0.05 (ANOVA). Significant differences in plasma α-tocopherol levels between experimental groups on day 0 and day 28 are designated as $^a$P <0.05 (SPANOVA) while differences in the levels between experimental groups on day 0 and day 56 are designated as $^y$P <0.05 (SPANOVA).

FIG. 11: Concentration of Tocotrienols in the Plasma of Control and Experimental Volunteers One hundred volunteers were randomly assigned in two groups i.e. control (received placebo) or experimental (received 400 mg TRF daily). Blood was drawn from both groups on day 0, day 28 and day 56. Plasma was isolated from the blood and prepared for HPLC analysis as described in the methods section. The plasma concentration of tocotrienols from this analysis is reported in µg/mL.

Significant difference in plasma alpha-tocotrienol concentration between control and experimental group on day 28 is shown as $^a$P <0.01 (ANOVA) while difference between control and experimental group on day 56 is shown as $^y$P <0.01 (ANOVA). Significant differences in plasma alpha-tocotrienol levels between experimental groups on day 0 and day 28 are designated as $^e$P <0.01 (SPANOVA) while differences in the levels between experimental groups on day 0 and day 56 are designated as $^e$P <0.01 (SPANOVA).

Significant difference in plasma gamma-tocotrienol concentration between control and experimental group on day 28 is shown as $^a$P <0.05 (ANOVA) while difference between control and experimental group on day 56 is shown as $^f$P <0.05 (ANOVA). Significant differences in plasma gamma-tocotrienol levels between experimental groups on day 0 and day 28 are designated as $^f$P <0.05 (SPANOVA) while differences in the levels between experimental groups on day 0 and day 56 are shown as $^\phi$P <0.05 (SPANOVA).

Significant difference in plasma delta-tocotrienol concentration between control and experimental group on day 28 is shown as $^\Psi$P<0.05 (ANOVA) while difference between control and experimental group on day 56 is shown as $^z$P <0.05 (ANOVA). Significant differences in plasma delta-tocotrienol levels between experimental groups on day 0 and day 28 are designated as $^x$P<0.05 (SPANOVA) while differences in the levels between experimental groups on day 0 and day 56 are shown as $^\pi$P <0.05 (SPANOVA).

Effect of TRF Supplementation on the Production of Cytokines by Mitogen or Antigen Stimulated PBMC Blood was drawn from all volunteers on day 0, 28 and 56 as described in the methods section. Peripheral blood mononuclear cells (PBMC) were isolated as described in section 3.4.8 and the leucocytes were cultured in the presence Con A, LPS or pure TT. The culture supernatant was harvested following 72 hours of culture and the amount of cytokines (IFN-γ, IL-4, IL-6 and IL-10) produced was quantified using ELISA. In this present invention, cytokine productions by PBMC following TT stimulation were only measure on day 28 and 56 i.e. before and after administration of the TT vaccine reported by Meydani et al. (1997). Baseline (day 0) levels of the cytokines following TT stimulation were reported to be similar to the levels on day 28 prior to the administration of TT vaccine in volunteers (Meydani et al., 1997). However, the production of cytokines by PBMCs following both Con A and LPS stimulation (non-specific mitogens) were measured on day 0, day 28 and day 56.

Effect of TRF Supplementation on the Production of IFN-γ by Con A- or TT-Stimulated PBMC FIG. 12 shows the production of IFN-γ by PBMC's of the volunteers in the control and experimental groups. The production of IFN-γ was significantly ($P<0.05$) enhanced by the Con A-stimulated PBMC on Day 56, i.e. after TT vaccination, when compared to that produced on day 0 or 28. The IFN-γ levels were only slightly higher on day 28 compared to day 0. In addition, the difference observed between the TRF and placebo group on day 28 was not statistically significant ($P>0.05$). On day 56 i.e. 28 days after the administration of the TT vaccine, the amount of IFN-γ produced was significantly ($P<0.02$) enhanced in PBMC 's of volunteers who received TRF-supplementation as compared with the corresponding placebo group.

The amount of IFN-γ produced by PBMC stimulated by the specific antigen, i.e. TT, was also determined (see FIG. 13). Most of the PBMC from the volunteers responded to stimulation with the TT on day 28 i.e. prior to the booster TT immunisation. This could be due to previous exposure to this antigen during childhood immunisation programmes. Following TT vaccination on day 56, the production of IFN-γ following in vitro TT stimulation was augmented in both TRF- and placebo-supplemented groups. However, the cytokine level was highly significant ($P<0.01$) in volunteers who received TRF-compared to placebo-supplementation.

Effect of TRF Supplementation on the Production of IL-4 by Con A- or TT-Stimulated PBMC As shown in FIG. 14, prior to the TT vaccination, PBMCs of the volunteers produced very low levels of IL-4 as compared to IFN-γ in Con A-stimulated cultures. One month after the TT vaccination (day 56), the levels of IL-4 were significantly ($P<0.05$) elevated as compared to day 0 and day 28 of the study in both TRF and placebo supplemented groups. However, the concentrations of IL-4 on Day 56 did not differ significantly ($P>0.05$) between the control and experimental groups.

The IL-4 levels in TT-stimulated PBMC cultures were assayed at two time points i.e. at four-week pre- and post-TT vaccination. PBMC stimulated by TT produced lower amounts of IL-4 as compared to Con A-stimulated PBMCs (see FIGS. 14 and 15). Prior to the TT vaccination i.e. on day 28, there was no statistically significant ($P>0.05$) difference in the amount of IL-4 produced by TT-stimulated human PBMCs from the TRF and placebo supplemented volunteers (see FIG. 15). In contrast, the IL-4 level was significantly ($P<0.05$) augmented following TT vaccination in volunteers who received TRF as compared to placebo on day 56 (see FIG. 15).

Effect of TRF Supplementation on the Production of IL-6 by LPS-Stimulated PBMC

It is well accepted that pro-inflammatory cytokines such as IL-6 and TNF-α are produced by macrophages to induce acute phase proteins following pathogen challenge (Levi et al., 2003). The LPS-stimulated PBMCs from volunteers produced high levels of IL-6 on day 0 and 28 of the study (see FIG. 16) in both control and experimental groups of volunteers. However, volunteers supplemented with TRF had significantly ($P<0.05$) lower production of IL-6 on day 56, i.e. one-month after the TT immunisation in comparison to volunteers who received placebo (see FIG. 16).

The amount of IFN-γ produced by Con A-stimulated PBMC isolated from peripheral blood of control and experimental groups were determined. The amount of IFN-γ produced on day 0 (baseline), day 28 (four-weeks of placebo or TRF supplementation and before TT vaccination) and day 56 (eight-weeks of placebo or TRF supplementation and four-weeks after TT vaccination) were determined. Statistically significant differences were observed in IFN-γ levels produced by Con A-stimulated PBMCs from control and experimental volunteers on day 56. Significant difference between control and experimental groups on day 56 is shown as $^eP <0.02$ (ANOVA). Significant differences between control group on day 56 as compared to day 0 and day 28 are designated as $^qP <0.05$ (SPANOVA) while differences in the levels between experimental group on day 56 as compared to day 0 and day 28 are shown as $^aP <0.05$ (SPANOVA).

The amount of IFN-γ produced by TT-stimulated PBMC isolated from peripheral blood of volunteers from the control (placebo-treated) and experimental groups were determined as described in the methods section. The amount of IFN-γ produced on day 28 (four-weeks of placebo or TRF supplementation and before TT vaccination) and day 56 (eight-weeks of placebo or TRF supplementation and four-weeks after TT vaccination) were determined.

Significant difference in TT specific IFN-γ levels between control and experimental group on day 28 is shown as $^eP <0.05$ (ANOVA) while difference between control and experimental group on day 56 is shown as $^qP <0.01$ (ANOVA). Significant differences between control groups on day 28 and day 56 are designated as $^xP<0.05$ (SPANOVA) while differences in the levels between experimental groups on day 28 and day 56 are shown as $^aP <0\,01$ (SPANOVA).

The amount of IL-4 produced by Con A-stimulated PBMC isolated from peripheral blood of volunteers of the control (placebo-treated) and experimental groups. The amount of IL-4 produced on day 0 (baseline), day 28 (four-weeks of placebo or TRF supplementation and before TT vaccination) and day 56 (eight-weeks of placebo or TRF supplementation and four-weeks after TT vaccination) were determined.

Significant differences between control groups on day 56 as compared to day 0 and day 28 are designated as $^eP <0.05$ (SPANOVA) while differences in the levels between experimental groups on day 56 as compared to day 0 and day 28 are shown as $^qP <0.05$ (SPANOVA).

Effect of TRF Supplementation on the Production of IL-10 by Con A- or TT-Stimulated PBMC Interleukin-10 is a well-documented immunosuppressive cytokine that can reduce the expression of co-stimulatory molecules on antigen-presenting cells (Corinti et al., 2001), thereby inhibiting the antigen-presenting capacity of dendritic cells (DC) (Thomssen et al., 1995). In this present invention, all volunteers showed detectable levels of IL-10 production by Con A-stimulated PBMCs on days 0, 28 and 56 (see FIG. 17).

Although the levels of IL-10 produced increased slightly from the baseline to day 56 of the study, the levels were insignificant ($P>0.05$) and no significant ($P>0.05$) changes in the productions of IL-10 were observed between the TRF and placebo groups (see FIG. 17). As shown in FIG. 18, PBMCs stimulated by TT also showed a slight augmentation in the production of IL-10 in TRF supplemented group on day 28 and 56 when compared to the placebo group. However the changes in the cytokine levels were insignificant ($P>0.05$).

The amount of IL-10 produced by Con A-stimulated PBMC isolated from peripheral blood of volunteers from the control (placebo-treated) and experimental groups. The amount of IL-10 produced on day 0 (baseline), day 28 (four-weeks of placebo or TRF supplementation and before TT vaccination) and day 56 (eight-weeks of placebo or TRF supplementation and four-weeks after TT vaccination) were determined. The differences in the level of IL-10 production between TRF and placebo supplemented groups on days 0, 28 and 56 were not statistically significant (SPANOVA).

The amount of IL-10 produced by TT-stimulated PBMC isolated from peripheral blood of volunteers from the control (placebo-treated) and experimental groups were determined as described in the methods section. The amount of IL-10 produced on day 28 (four-weeks of placebo or TRF supplementation and before TT vaccination) and day 56 (eight-weeks of placebo or TRF supplementation and four-weeks after TT vaccination) were determined.

The differences in the levels of TT specific IL-10 production between TRF and placebo supplemented groups on days 28 and 56 were not statistically significant (SPANOVA).

Anti-Tetanus Antibody Levels in Plasma Following TRF Supplementation and TT Vaccination The effects of TRF supplementation on the production of total Ig in the plasma of human volunteers vaccinated with TT were investigated. The amount of anti-TT antibodies produced are used as a marker for the humoral arm of the immune response. Detectable amounts of total Ig of anti-TT antibodies were present on day 0 and day 28 of the study but the titres were relatively low as compared to that observed after the TT vaccination i.e. day 56 (see FIG. 19). The anti-TT Ig titres significantly increased one-month after the TT vaccination in both the TRF and placebo groups (see FIG. 19).

The anti-TT Ig titres observed on day 56 in both groups were significantly (P<0.05) higher compared to day 0 and 28. Volunteers supplemented with TRF showed a significantly (P<0.05) higher anti-TT Ig production on day 56 compared to those supplemented with placebo.

An enhanced anti-TT IgG production was also observed in the TRF-supplemented group after TT-vaccination i.e. on day 56 (see FIG. 20). The mean level of anti-TT IgG in the study population prior to the TT vaccination was 0.79 IU/mL and the levels rose significantly (P<0.05) one-month after the TT vaccination in both TRF and placebo supplemented volunteers. On day 56, the mean anti-TT IgG levels in the placebo- and TRF-supplemented groups were 1.30 IU/mL and 1.93 IU/mL, respectively and the levels were significantly (P<0.05) higher in the TRF group as compared to placebo (see FIG. 20). Volunteers in both groups have achieved a protective anti-TT response after vaccination, which is defined as anti-tetanus antibody level of ≥0.85 IU/mL (Kilian and Nielsen, 1989). Blood was drawn from volunteers from the control (placebo-supplemented) and experimental (TRF-supplemented) groups on day 0, 28 and 56.

A booster dose of the TT vaccine was administered i.m. on day 28. Plasma levels of total Ig anti-TT were determined by ELISA. Significant differences in anti-TT Ig titres between placebo (control) group on day 56 as compared to day 0 and day 28 are designated as $^*P$ <0.05 (SPANOVA) while differences in the titres between experimental (TRF) group on day 56 as compared to day 0 and day 28 are shown as $^\#P$ <0.05 (SPANOVA).

Significant difference in anti-TT Ig titres between control and experimental groups on day 56 is shown as $^\varphi P$ <0.5 (ANOVA).

Blood was drawn from volunteers from the control (placebo-supplemented) and experimental (TRF-supplemented) groups on day 0, 28 and 56. A booster dose of the TT vaccine was administered i.m. on day 28. Plasma levels of anti-TT IgG were determined by ELISA. Significant differences in IgG concentrations between placebo (control) group on day 56 as compared to day 0 and day 28 are designated as $^*P$ <0.05 (SPANOVA) while differences in the IgG levels between experimental (TRF) group on day 56 as compared to day 0 and day 28 are shown as $^\#P$ <0.05 (SPANOVA). Significant difference in the levels between control and experimental groups on day 56 is shown as $^\varphi P$ <0.05 (ANOVA).

FIG. 21: Scatter plots comparing the percentages of total T-lymphocytes between healthy volunteers supplemented with either TRF or placebo. Blood was drawn from volunteers on day 0 (A), day 28 (B) and day 56 (C). The lymphocytes were stained with antibodies to CD3 antigen and analysed with flow cytometry. The difference in total T-cells percentages between TRF and placebo groups were not significant (SPANOVA) at each time point i.e. day 0, 28 and 56. The x-axis shows n=50 in the TRF group and n=50 in the placebo group, making the total n=100.

The invention claimed is:

1. A kit for supplementing an immune response provided by a vaccine, said kit comprising:
   a formulation comprising Vitamin E wherein the vitamin E consists of Tocotrienol Rich Fraction (TRF), which consists of about 32% alpha-tocopherol, about 25% alpha-tocotrienol, about 29% gamma-tocotrienol, and about 14% delta-tocotrienol; and
   tetanus toxoid vaccine.

2. A method of manufacturing a medication for supplementing an immune response provided by a vaccine, the method comprising:
   providing tetanus toxoid vaccine; and
   providing a formulation comprising vitamin E which supplements an immune response provided by the vaccine when both the vaccine and formulation are administered to a user during use;
   wherein the vitamin E consists of Tocotrienol Rich Fraction (TRF), which consists of about 32% alpha-tocopherol, about 25% alpha-tocotrienol, about 29% gamma-tocotrienol, and about 14% delta-tocotrienol.

3. The method according to claim 2, wherein the medication is adapted for strengthening the immune response in a mammal.

4. An article of manufacture comprising:
   packaging material contained within which is a formulation effective to strengthen the immune response to tetanus toxoid vaccine in a person, wherein:
   the packaging material comprises a label which indicates that the formulation can be used to strengthen the immune response; and
   tetanus toxoid vaccine;
   wherein said formulation is a pharmaceutical composition comprising Vitamin E, wherein the vitamin E consists of Tocotrienol Rich Fraction (TRF), which consists of about 32% alpha-tocopherol, about 25% alpha-tocotrienol, about 29% gamma-tocotrienol, and about 14% delta-tocotrienol.

* * * * *